(12) United States Patent
Godwin

(10) Patent No.: US 8,618,333 B2
(45) Date of Patent: Dec. 31, 2013

(54) REAGENTS AND METHOD FOR CONJUGATING BIOLOGICAL MOLECULES

(75) Inventor: Antony Godwin, London (GB)

(73) Assignee: Polytherics Limited, London (GB)

(*) Notice: Subject to any disclaimer, the term of this patent is extended or adjusted under 35 U.S.C. 154(b) by 250 days.

(21) Appl. No.: 13/175,820

(22) Filed: Jul. 1, 2011

(65) Prior Publication Data

US 2011/0262994 A1 Oct. 27, 2011

Related U.S. Application Data

(63) Continuation of application No. 13/055,455, filed as application No. PCT/GB2009/001764 on Jul. 17, 2009.

(30) Foreign Application Priority Data

Jul. 21, 2008 (GB) .................................... 0813339.9
Apr. 2, 2009 (GB) .................................... 0905762.1

(51) Int. Cl.
*C07C 49/794* (2006.01)

(52) U.S. Cl.
USPC .......................................... 568/335; 568/308

(58) Field of Classification Search
None
See application file for complete search history.

(56) References Cited

U.S. PATENT DOCUMENTS

| | | | |
|---|---|---|---|
| 5,414,135 A | 5/1995 | Snow et al. |
| 5,446,090 A | 8/1995 | Harris |
| 5,739,208 A | 4/1998 | Harris |
| 6,677,438 B1 | 1/2004 | Garnett et al. |
| 7,595,292 B2 | 9/2009 | Brocchini et al. |
| 7,939,630 B2 | 5/2011 | Brocchini et al. |
| 2005/0209416 A1 | 9/2005 | Harris |
| 2006/0147443 A1 | 7/2006 | Schense et al. |
| 2006/0210526 A1 | 9/2006 | Brocchini et al. |
| 2009/0298154 A1 | 12/2009 | Brocchini et al. |
| 2011/0136723 A1 | 6/2011 | Godwin |
| 2011/0182855 A1 | 7/2011 | Brocchini et al. |
| 2011/0262994 A1 | 10/2011 | Godwin |
| 2012/0014905 A1 | 1/2012 | Godwin et al. |

FOREIGN PATENT DOCUMENTS

| | | |
|---|---|---|
| WO | 95/13312 | 5/1995 |
| WO | 95/34326 | 12/1995 |
| WO | 99/01469 | 1/1999 |
| WO | 2004/060965 | 7/2004 |
| WO | 2005/007197 | 1/2005 |
| WO | 2006/067221 | 6/2006 |

OTHER PUBLICATIONS

Balan, Sibu et al; "Site specific pegylation of prtein disulfide bonds using a three carbon bridge." Bioconjugate Chem. (2007) 18(1) p. 61-76, published online Nov. 29, 2006.*

March "The Michael reaction" in *Advanced Organic Chemistry, Reactions, Mechanisms, and Structure*, 3rd Ed., John Wiley & Sons, pp. 711-712 (1985).
Examination Report for related application EP 09784718.0 and claims pending therein, all pages, mailed May 7, 2012.
Brocchini et al. "PEGylation of native disulfide bonds in proteins" *Nature Protocols*, vol. 1, No. 5, pp. 2241-2252 (Dec. 2006).
Brocchini et al. "Disulfide bridge based PEGylation of proteins" *Adv. Drug Delivery Rev.*, vol. 60, No. 1, pp. 3-12 (Jan. 2008).
Dewick "Nucleophilic reactions of carbonyl groups" in *Essentials of Organic Chemistry*, Wiley, pp. 221-222 and 235 (2006).
Hermanson "NHS esters" in *Bioconjugate Techniques, 2nd Ed.*, Elsevier, pp. 171-172 (2008).
Written Opinion for PCT/GB2009/001764, seven pages, mailed Dec. 9, 2009.
Drotleff et al. "Biomimetic polymers in pharmaceutical and biomedical sciences" Eur. J. Pharm. Biopharm., vol. 58, No. 2, pp. 385-407 (Sep. 2004).
Guan et al. "An economical and convenient synthesis of vinyl sulfones" Synthesis, No. 10, pp. 1465-1470 (Sep. 2007).
Harris "Polyethylene glycol and derivatives for advanced PEGylation" in *Nektar Advanced PEGylation Catalog*, pp. 1-30 (2005-2006).
Mather et al. "Michael addition reactions in macromolecular design for emerging technologies" Frog. Polym. Sci., vol. 31, No. 5, pp. 487-531 (May 2006).
Metters & Hubbell "Network formation and degradation behavior of hydrogels formed by Michael-type addition reactions" Biomacromol, vol. 6, No. 1, pp. 290-301 (Jan. 2005).
Morpurgo et al. "Preparation and characterization of poly(ethylene glycol) vinyl sulfone" Bioconj. Chem., vol. 7, No. 3, pp. 363-368 (May-Jun. 1996).
Won "Synthesis of heterobifunctional poly(ethylene glycol) containing an acryloyl group at one end and an isocyanate group at the other end" Polymer Bull., vol. 52, No. 2, pp. 109-115 (Aug. 2004).
Hunter & Renfrew "The chemistry of activated π-bonds as reactive groups" in *Reactive Dyes for Textile Fibres*, Woodhead Publ. pp. 1-28 (1999).
Messinger & Borchert-Bremer "Kinetische untersuchungen an aktivierten sulfonen" Arch. Pharm. (Weinheim) vol. 316, No. 8, pp. 657-663 (Aug. 1983).

(Continued)

*Primary Examiner* — Cecilia J Tsang
*Assistant Examiner* — Fred Reynolds
(74) *Attorney, Agent, or Firm* — Nixon & Vanderhye PC

(57) ABSTRACT

A compound of the general formula X-[Q-W—(CH═CH)$_n$—(CH$_2$)$_2$-L]$_m$ (I) in which X represents a polymer; Q represents a linking group; W represents an electron-withdrawing group; n represents 0 or an integer of from 1 to 4; L represents a leaving group; and m represent an integer of from 1 to 8. The compounds find use in the conjugation of biological molecules.

9 Claims, 16 Drawing Sheets

(56) References Cited

OTHER PUBLICATIONS

Figure 1:
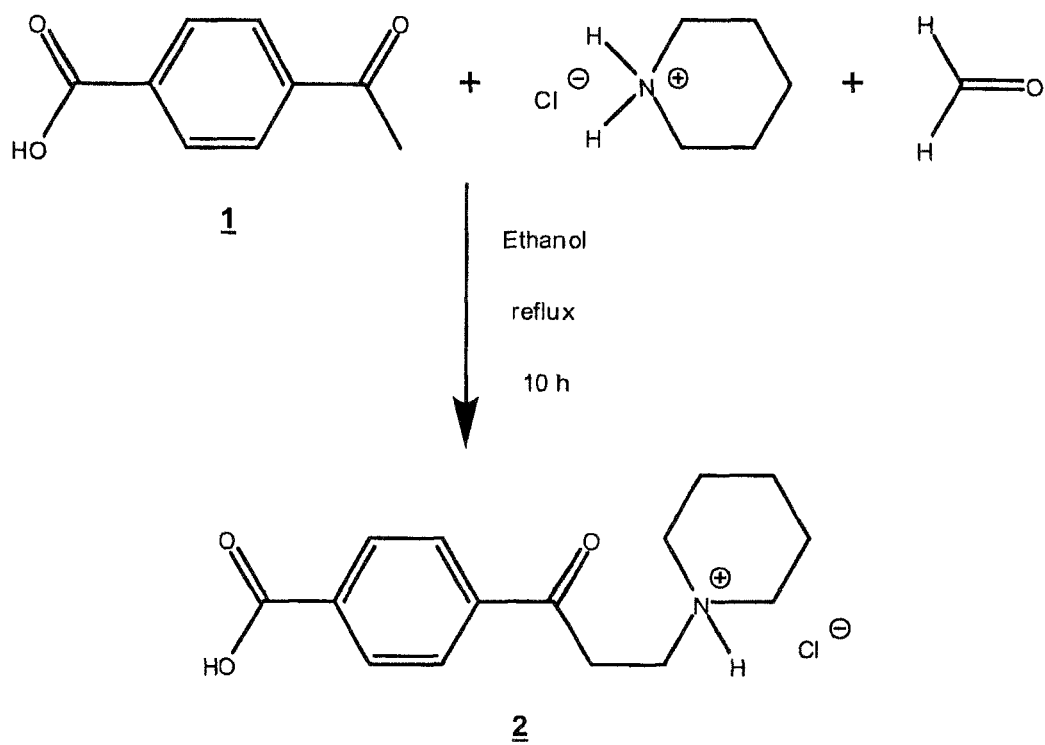

Roberts et al. "Chemistry for peptide and protein PEGylation" Adv. Drug Deliv. Rev., vol. 54, No. 4, pp. 459-476 (Jun. 2002).
Int'l Search Report for PCT/GB2009/001764, four pages, mailed Dec. 9, 2009.
Written Opinion for PCT/GB2008/001764, seven pages, mailed Dec. 9, 2009.
Int'l Preliminary Report on Patentability for PCT/GB2009/001764, seven pages, mailed Jan. 25. 2011.

* cited by examiner

REAGENTS AND METHOD FOR CONJUGATING BIOLOGICAL MOLECULES

This application is a continuation of application Ser. No. 13/055,455, filed Jan. 21, 2011, now pending; which is a national stage of Intl Application No. PCT/GB2009/001764, under 35 U.S.C. 371, filed Jul. 17, 2009; the entire contents of each of which are hereby incorporated by reference.

This invention relates to novel reagents and a novel method for conjugating biological molecules, especially proteins and peptides.

Many therapeutically active molecules, for example proteins, do not possess the properties required to achieve efficacy in clinical medical use. For example, many native proteins do not make good medicines because upon administration to patients there are several inherent drawbacks that include: (1) proteins are digested by many endo- and exo-peptidases present in blood or tissue; (2) many proteins are immunogenic to some extent; and (3) proteins can be rapidly excreted by kidney ultrafiltration and by endocytosis. Some molecules which might find utility as active therapeutic agents in medicines are systemically toxic or lack optimal bioavailability and pharmacokinetics. When proteins clear from the blood circulation quickly they typically have to be administered to the patient frequently. Frequent administration further increases the risk of toxicity, especially immunologically derived, toxicities.

Water soluble, synthetic polymers, particularly polyalkylene glycols, are widely used to conjugate therapeutically active molecules such as proteins, peptides and low molecular weight drugs. These therapeutic conjugates have been shown to alter pharmacokinetics favourably by prolonging circulation time and decreasing clearance rates, decreasing systemic toxicity, and in several cases, displaying increased clinical efficacy. The process of covalently conjugating polyethylene glycol, PEG, to proteins is commonly known as "PEGylation".

It is important for optimised efficacy and to ensure dose to dose consistency that the number of conjugated polymer molecules per protein is the same for each molecule, and that each polymer molecule is specifically covalently conjugated to the same amino acid residue in each protein molecule. Non-specific conjugation at sites along a protein molecule results in a distribution of conjugation products and, frequently, unconjugated protein, to give a complex mixture that is difficult and expensive to purify.

For thiol specific conjugation, PEGylation reagents having a PEG chain terminated on one end with a maleimide group are commonly used. Such reagents are described in many publications, for example WO 2004/060965. Maleimide-terminated reagents are commercially available. However, many PEG-maleimides are hydrolytically unstable during storage and conjugation to a drug candidate. Specifically, a substantial degree of hydrolysis of the maleimide ring occurs, both prior to and after conjugation.

We have now found a class of PEGylation reagents which can be used to conjugate molecules including proteins and peptides to polymers via a single nucleophilic residue, for example a thiol group, and which have advantages over such commercial reagents.

Accordingly, the present invention provides a process for the conjugation of a molecule containing a thiol or amino group to a polymer, which comprises reacting said molecule with a compound of the general formula:

$$X-[Q-W-(CH=CH)_n-(CH_2)_2-L]_m \quad (I)$$

in which X represents a polymer; Q represents a linking group; W represents an electron-withdrawing group; n represents 0 or an integer of from 1 to 4; L represents a leaving group; and m represent an integer of from 1 to 8.

The direct product resulting from the process of the invention may be generally represented by the general formula:

$$X-[Q-W-(CH=CH)_n-(CH_2)_2-Z]_m \quad (IIa)$$

in which X, Q, W n and m have the meanings given above, and Z represents said molecule conjugated via a thiol or amino group. If desired, this resulting compound of formula IIa can be converted into any other desired product. Specifically, a resulting compound of the general formula IIa may be converted into a compound of the general formula II $$X-[Q-W'-(CH=CH)_n-(CH_2)_2-Z]_m \quad (II)$$

in which W' represents an electron-withdrawing moiety or a moiety preparable by reduction of an electron-withdrawing moiety.

The compounds of the general formula (I) are novel, and the invention therefore also provides these compounds per se. Particularly preferred novel compounds of the formula (I) are those of the formula (Ia) as defined, below.

The compounds of the general formula (II) are also novel, and the invention therefore also provides these compounds per se. Particularly preferred novel compounds of the formula (II) are those of the formula (IIb) as defined below.

m represents an integer from 1 to 8, for example 1 to 6, preferably 1 to 4, for example 1. Where m is 1, a single molecule is conjugated to the polymer. When m is greater than one, the conjugation of more than one molecule to a polymer may be accomplished. From 2 to 8 groups -Q-W'—(CH=CH)$_n$—(CH$_2$)$_2$—Z or -Q-W—(CH=CH)$_n$—(CH$_2$)$_2$-L are attached to the polymer, and the variables Q, W, W', n, L and Z may be the same or different for each such group. Multi-functional polymer compounds are available, for example, multiple groups may be attached using as starting material the multi-arm compounds available from NOF under the Trade Mark "Sunbright": e.g. the 4-arm products have the formula C[CH$_2$O(CH$_2$CH$_2$O)$_n$—Y]$_4$ where Y may be one of a number of different end groups. Multimeric conjugates can result in synergistic and additive benefits. For example, if m is 1, the resulting conjugate must have an end group on the end of the PEG chain remote from the conjugated molecule. This is commonly an alkoxy or similar group, and it has been suggested that such groups may lead to undesired immunogenic effects when used for pharmaceutical applications. If m is greater than 1, a conjugated molecule can be attached to both ends of the PEG chain, dispensing with the need for an end group such as alkoxy.

A polymer X may for example be a polyalkylene glycol, a polyvinylpyrrolidone, a polyacrylate, for example polyacryloyl morpholine, a polymethacrylate, a polyoxazoline, a polyvinylalcohol, a polyacrylamide or polymethacrylamide, for example polycarboxymethacrylamide, or a HPMA copolymer. Additionally X may be a polymer that is susceptible to enzymatic or hydrolytic degradation. Such polymers, for example, include polyesters, polyacetals, poly(ortho esters), polycarbonates, poly(imino carbonates), and polyamides, such as poly(amino acids). A polymer X may be a homopolymer, random copolymer or a structurally defined copolymer such as a block copolymer. For example X may be a block copolymer derived from two or more alkylene oxides, or from poly(alkylene oxide) and either a polyester, polyacetal, poly(ortho ester), or a poly(amino acid). Polyfunctional polymers that may be used include copolymers of divinylether-maleic anhydride and styrene-maleic anhydride.

Naturally occurring polymers may also be used, for example polysaccharides such as chitin, dextran, dextrin, chitosan, starch, cellulose, glycogen, poly(sialylic acid) and derivatives thereof. A protein may be used as the polymer. This allows conjugation of one protein, for example an antibody or antibody fragment, to a second protein, for example an enzyme or other active protein. Also, if a peptide containing a catalytic sequence is used, for example an O-glycan acceptor site for glycosyltransferase, it allows the incorporation of a substrate or a target for subsequent enzymatic reaction. Poly(amino acid)s such as polyglutamic acid or polyglycine may also be used, as may hybrid polymers derived from natural monomers such as saccharides or amino acids and synthetic monomers such as ethylene oxide or methacrylic acid.

If the polymer is a polyalkylene glycol, this is preferably one containing $C_2$ and/or $C_3$ units, and is especially a polyethylene glycol. A polymer, particularly a polyalkylene glycol, may contain a single linear chain, or it may have branched morphology composed of many chains either small or large. The so-called Pluronics are an important class of PEG block copolymers. These are derived from ethylene oxide and propylene oxide blocks. Substituted polyalkylene glycols, for example methoxypolyethylene glycol, may be used. In a preferred embodiment of the invention, a single-chain polyethylene glycol is initiated by a suitable group, for example an alkoxy, e.g. methoxy, aryloxy, carboxy or hydroxyl group, and is connected at the other end of the chain to the linker group Q.

The polymer X may optionally be derivatised or functionalised in any desired way. Reactive groups may be linked at the polymer terminus or end group, or along the polymer chain through pendent linkers; in such case, the polymer is for example a polyacrylamide, polymethacrylamide, polyacrylate, polymethacrylate, or a maleic anhydride copolymer. Such functionalised polymers provide a further opportunity for preparing multimeric conjugates (i.e. conjugates in which the polymer, is conjugated to more than one molecule). If desired, the polymer may be coupled to a solid support using conventional methods.

The optimum molecular weight of the polymer will of course depend upon the intended application. Preferably, the number average molecular weight is in the range of from 250 g/mole to around 75,000 g/mole. When the compound of the general formula II is intended for medical use and is intended to leave the circulation and penetrate tissue, for example for use in the treatment of inflammation caused by malignancy, infection or autoimmune disease, or by trauma, it may be advantageous to use a lower molecular weight polymer in the range 2000-30,000 g/mole. For applications where the compound of the general formula II is intended to remain in circulation it may be advantageous to use a higher molecular weight polymer, for example in the range of 20,000-75,000 g/mole.

The polymer to be used should be selected so the conjugate is soluble in the solvent medium for its intended use. For biological applications, particularly for diagnostic applications and therapeutic applications for clinical therapeutic administration to a mammal, the conjugate will be soluble in aqueous media. However, many biological molecules, for example proteins such as enzymes, have utility in industry, for example to catalyze chemical reactions. For conjugates intended for use in such applications, it may be necessary that the conjugate be soluble in either or both aqueous and organic media. The polymer should of course not unduly impair the intended function of the molecule to be conjugated.

Preferably the polymer is a synthetic polymer, and preferably it is a water-soluble polymer. The use of a water-soluble polyethylene glycol is particularly preferred for many applications.

A linking group Q may for example be a direct bond, an alkylene group (preferably a $C_{1-10}$ alkylene group), or an optionally-substituted aryl or heteroaryl group, any of which may be terminated or interrupted by one or more oxygen atoms, sulphur atoms, —NR groups (in which R represents a hydrogen atom or an alkyl (preferably $C_{1-6}$alkyl), aryl (preferably phenyl), or alkyl-aryl (preferably $C_{1-6}$alkyl-phenyl) group), keto groups, —O—CO— groups, —CO—O— groups, —O—CO—O, —O—CO—NR—, —NR—CO—O—, —CO—NR— and/or —NR.CO— groups. Such aryl and heteroaryl groups Q form one preferred embodiment of the invention. Suitable aryl groups include phenyl and naphthyl groups, while suitable heteroaryl groups include pyridine, pyrrole, furan, pyran, imidazole, pyrazole, oxazole, pyridazine, primidine and purine. Especially suitable linking groups Q are heteroaryl or, especially, aryl groups, especially phenyl groups, terminated adjacent the polymer X by an —NR.CO— group. The linkage to the polymer may be by way of a hydrolytically labile bond, or by a non-labile bond.

Substituents which may be present on an optionally substituted aryl or heteroaryl group include for example one or more of the same or different substituents selected from alkyl (preferably $C_{1-4}$alkyl, especially methyl, optionally substituted by OH or $CO_2H$), —CN, —$NO_2$, —$CO_2R$, —COH, —$CH_2OH$, —COR, —OR, —OCOR, —$OCO_2R$, —SR, —SOR, —$SO_2R$, —NHCOR, —NRCOR, $NHCO_2R$, —$NR.CO_2R$, —NO, —NHOH, —NR.OH, —C=N—NH-COR, —C=N—NR.COR, —$N^+R_3$, —$N^+H_3$, —$N^+HR_2$, —$N^+H_2R$, halogen, for example fluorine or chlorine, —C≡CR, —C=$CR_2$ and —C=CHR, in which each R independently represents a hydrogen atom or an alkyl (preferably $C_{1-6}$alkyl), aryl (preferably phenyl), or alkyl-aryl (preferably $C_{1-6}$alkyl-phenyl) group. The presence of electron withdrawing substituents is especially preferred. Preferred substituents include for example CN, $NO_2$, —OR, —OCOR, —SR, —NHCOR, —NR.COR, —NHOH and —NR.COR.

W may for example represent a keto group CO, an ester group —O—CO— or a sulphone group —$SO_2$—, and W' may represent such a group or a group obtained by reduction of such a group, e.g. a CH.OH group, an ether group CH.OR, an ester group CH.O.C(O)R, an amine group $CH.NH_2$, CH.NHR or $CH.NR_2$, or an amide CH.NHC(O)R or CH.N(C(O)R)$_2$.

Preferably n is 0.

A leaving group L may for example represent —SR, —$SO_2R$, —$OSO_2R$, —$N^+R_3$, —$N^+HR_2$, —$N^+H_2R$, halogen, or —OØ, in which R has the meaning given above, and Ø represents a substituted aryl, especially phenyl, group, containing at least one electron withdrawing substituent, for example —CN, —$NO_2$, —$CO_2R$, —COH, —$CH_2OH$, —COR, —OR, —OCOR, —$OCO_2R$, —SR, —SOR, —$SO_2R$, —NHCOR, —NRCOR, —$NHCO_2R$, —NR'$CO_2R$, —NO, —NHOH, —NR'OH, —C=N—NH-COR, —C=N—NR'COR, —$N^+R_3$, —$N^+HR_2$, —$N^+H_2R$, halogen, especially chlorine or, especially, fluorine, —C≡CR, —C=$CR_2$ and —C=CHR, in which each R independently has one of the meanings given above.

If m represents an integer of from 2 to 8, different L groups may be present if desired. This provides an opportunity, by selecting L groups of different reactivity, to conjugate different molecules to the polymer X in successive reactions.

Preferably the process according to the invention uses a reagent of the general formula:

$$X-[NH-CO-Ar-W-(CH=CH)_n-(CH_2)_2-SO_2R']_m \quad \text{(Ia)}$$

in which Ar represents an unsubstituted or substituted aryl group, especially a phenyl group, in which the optional substituents are selected from those mentioned above for an aryl group contained in linking group Q; R' represents a hydrogen atom or an optionally substituted alkyl (preferably $C_{1-6}$alkyl), aryl (preferably phenyl), or alkyl-aryl (preferably $C_{1-6}$alkyl-phenyl) group; and W and m have the meanings given above; to produce a novel conjugate of the general formula:

$$X-[NH-CO-Ar-W'-(CH=CH)_n-(CH_2)_2-Z]_m \quad \text{(IIb)}$$

In these preferred compounds Ia and IIb, preferably n is 0, and preferably m represents an integer of from 1 to 4, especially 1. Preferably each of W represents a CO group, and W' represents a CO group or a CH.OH group. Preferably R' represents an optionally substituted alkyl group, for example an optionally hydroxy substituted $C_{1-4}$alkyl group such as —$CH_2CH_2OH$, or, especially, a $C_{1-4}$alkyl-aryl group, especially p-tolyl. Preferably Ar is an unsubstituted phenyl group. Preferably X is a polyalkylene glycol, especially polyethylene glycol.

The compounds of formula I, and especially those of formula Ia, are believed to be surprisingly stable, and also have high reactivity towards molecules containing a thiol or amino group. It is believed that the conjugation process according to the invention proceeds via the formation of an intermediate compound of the general formula $$X-[Q-W-(CH=CH)_n-CH=CH_2]_m \quad \text{V}$$

in which X, Q, W, n and m have the meanings given above.

The molecule to be conjugated by the process of the present invention may be any desired molecule. It may for example be a naturally-occurring molecule or a molecule derived from a naturally occurring molecule, or it may be any molecule having biological activity, for example any drug, provided that it contains a thiol (—SH) or amino (—NHR) group. For example, it may be a protein or a peptide: throughout this specification, the term "protein" will be used for convenience, and except where the context requires otherwise, references to "protein" should be understood to be references to "protein or peptide".

The thiol or amino group through which the molecule is linked is a nucleophile capable of reacting with the reagent I, with, elimination of the leaving group L. Such groups may be present in a native biological molecule, or may be introduced into a biological molecule prior to conjugation.

Two thiol groups may be generated by reduction of a natural or engineered disulfide (cysteine) bridge, which may be intrachain or interchain. A biological molecule can contain one or a multiplicity of disulfide bridges, and reduction to give free sulfhydral moieties can be conducted to reduce one or a multiplicity of disulfide bridges. Depending on the extent of disulfide reduction and the stoichiometry of the polymeric conjugation reagent that is used, it is possible to conjugate one or a multiplicity of polymer molecules to the biological molecule. Immobilised reducing agents may be used if it is desired to reduce less than the total number of disulfides, as can partial reduction using different reaction conditions or the addition of denaturants.

Alternatively a thiol group can be a single cysteine residue or other thiol group not originally derived from a disulfide bridge. A single cysteine may be introduced by synthetic means to provide a suitable point of attachment. Such a procedure is particularly useful for the conjugation of peptides.

Amine groups may for example be lysine or histidine residues. These may be present in a native biological molecule, or introduced synthetically. For example, a histidine residue might be introduced by way of a his-tag, a short chain of contiguous histidine residues, for example containing up to 12 histidine residues but typically containing 5 or 6 residues, attached by synthetic methods to a protein. His-tags bind strongly to nickel and cobalt, enabling them to be bound to a nickel- or cobalt-containing column used in the separation process known as immobilized-metal affinity chromatography. His-tags are widely used, being attached to a wide range of proteins and peptides to enable them or products derived therefrom to be separated from mixtures at a future date.

Where the molecule is a protein, it may for example be a peptide, polypeptide, antibody, antibody fragment, enzyme, cytokine, chemokine, receptor, blood factor, peptide hormone, toxin, transcription protein, or multimeric protein.

The following gives some specific proteins which may have utility in the present invention, depending upon the desired application. Enzymes include carbohydrate-specific enzymes, proteolytic enzymes and the like. Enzymes of interest, for both industrial (organic based reactions) and biological applications in general and therapeutic applications in, particular include the oxidoreductases, transferases, hydrolases, lyases, isomerases and ligases disclosed by U.S. Pat. No. 4,179,337. Specific enzymes of interest include asparaginase, arginase, adenosine deaminase, superoxide dismutase, catalase, chymotrypsin, lipase, uricase, bilirubin oxidase, glucose oxidase, glucuronidase, galactosidase, glucocerbrosidase, glucuronidase, and glutaminase.

The proteins used in compounds of the general formula I include for example blood proteins such as albumin, transferring, Factor VII, Factor VIII or Factor IX, von Willebrand factor, insulin, ACTH, glucagen, somatostatin, somatotropins, thymosin, parathyroid hormone, pigmentary hormones, somatomedins, erythropoietin, luteinizing hormone, hypothalamic releasing factors, antidiuretic hormones, prolactin, interleukins, interferons, colony stimulating factors, hemoglobin, cytokines, antibodies, antibody fragments, chorionicgonadotropin, follicle-stimulating hormone, thyroid stimulating hormone and tissue plasminogen activator.

Certain of the above proteins such as the interleukins, interferons and colony stimulating factors also exist in non-glycosylated form, usually the result of preparation by recombinant protein techniques. The non-glycosylated versions may be used in the present invention.

Other proteins of interest are allergen proteins disclosed by Dreborg et al Crit. Rev. Therap. Drug Carrier Syst. (1990) 6 315-365 as having reduced allergenicity when conjugated with a polymer such as poly(alkylene oxide) and consequently are suitable for use as tolerance inducers. Among the allergens disclosed are Ragweed antigen E, honeybee venom, mite allergen and the like.

Glycopolypeptides such as immunoglobulins, ovalbumin, lipase, glucocerebrosidase, lectins, tissue plasminogen activator and glycosilated interleukins, interferons and colony stimulating factors are of interest, as are immunoglobulins such as IgG, IgE, IgM, IgA, IgD and fragments thereof.

Of particular interest are receptor and ligand binding proteins and antibodies and antibody fragments which are used in clinical medicine for diagnostic and therapeutic purposes. The antibody may be used alone or may be covalently conjugated ("loaded") with another atom or molecule such as a radioisotope or a cytotoxic/antiinfective drug. Epitopes may be used for vaccination to produce an immunogenic polymer-protein conjugate.

Biological molecules may be derivatised or functionalised if desired. In particular, prior to conjugation, the molecule, for example a native protein, may have been reacted with various blocking groups to protect sensitive groups thereon; or it may have been previously conjugated with one or more polymers or other molecules, either using the process of this invention or using an alternative process.

The molecule may be a synthetic molecule of relatively low molecular weight. It may, for example, be any drug for which conjugation provides advantages. For many such molecules, it will be necessary to insert a suitable linker carrying thiol or amino group to enable it to be conjugated to the reagent according to the invention. Typical drugs include for example captopril, amphotericin B, camptothecin, taxol, irinotecan and its derivatives such as SN38, docetaxol, and ribavirin.

Other molecules of interest which may be conjugated using the process of the invention include those listed in WO 2004/060965.

The process according to the invention may be carried out in a solvent or solvent mixture in which all reactants are soluble. The molecule to be conjugated, for example a protein, may be allowed to react directly with the compound of the general formula I in an aqueous reaction medium. This reaction medium may also be buffered, depending on the pH requirements of the nucleophile (thiol or amine). The optimum pH for the reaction will in many cases be at least 6.0, typically between about 6.8 and about 8.5, for example about 7.0 to 8.0, preferably about 7.5-8.0, but in other cases pH's of as low as 4.0 may be used, particularly when conjugation to a polyhistidine tag is required, leading to a usable pH range of from 4.0 to 8.5. If it is preferred to generate the compound of the formula V above in situ in the presence of the molecule to be conjugated, a relatively high pH is suitably used throughout. Alternatively, if it is preferred to generate the compound of the formula V above in a separate step and subsequently add the molecule to be conjugate, the first step is suitably carried out at a relatively high pH (e.g. 7-5-8.0) while the subsequent step is suitably carried out at a lower pH (e.g. 6.0 to 6.5). It is an advantage of the reagents of the present invention that they may be used successfully over a relatively wide range of pH conditions.

Reaction temperatures between 3-37° C. are generally suitable: proteins may decompose, aggregate or denature impairing function and/or reaction efficiency if the conjugation reaction is conducted at a temperature where these processes may occur. Reactions conducted in organic media (for example THF, ethyl acetate, acetone) are typically conducted at temperatures up to ambient.

The molecule can be effectively conjugated with the desired reagent using a stoichiometric equivalent or a slight excess of reagent, unlike many other reagents. However, since the reagents do not undergo competitive reactions with aqueous media used to solvate for example proteins, it is possible to conduct the conjugation reaction with an excess stoichiometry of reagent. The excess reagent and the product can be easily separated by ion exchange chromatography during routine purification, or by separation using nickel if a his-tag is present.

Where the group through which the molecule is conjugated is a thiol group, the process according to the invention may be carried out by partially reducing a disulfide bond derived from two cysteine amino acids in the biological molecule in situ following which the reduced product reacts with the compound of formula (I). Disulfides can be reduced, for example, with dithiothreitiol, mercaptoethanol, or tris-carboxyethylphosphine using conventional methods.

The immediate product of the process according to the invention is a compound of the general formula II in which W' is an electron-withdrawing group. Such compounds have utility in themselves: because the process of the invention is reversible under suitable conditions, compounds of formula (II) in which W' is an electron-withdrawing moiety have utility in applications where release of the molecule from the conjugate is required, for example in direct clinical applications. An electron-withdrawing moiety W' may, however, be reduced to give a moiety which prevents release of the molecule, and such compounds will also have utility in many clinical, industrial and diagnostic applications.

Thus, for example, a moiety W' containing a keto group may be reduced to a moiety W' containing a CH(OH) group; an ether group CH.OR may be obtained by the reaction of a hydroxy group with an etherifying agent; an ester group CH.O.C(O)R may be obtained by the reaction of a hydroxy group with an acylating agent; an amine group $CH.NH_2$, $CH.NHR$ or $CH.NR_2$ may be prepared from a ketone or aldehyde by reductive amination); or an amide CH.NHC(O)R or $CH.N(C(O)R)_2$ may be formed by acylation of an amine. The use of a borohydride, for example sodium borohydride, sodium cyanoborohydride, potassium borohydride or sodium triacetoxyborohydride, as reducing agent is particularly preferred. Other reducing agents which may be used include for example tin(II) chloride, alkoxides such as aluminium alkoxide, and lithium aluminium hydride.

A compound of the general formula (I) may be prepared by reacting a compound of the general formula

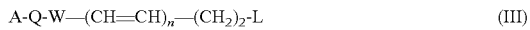

$$A-Q-W-(CH=CH)_n-(CH_2)_2-L \qquad (III)$$

in which Q, W, n and L have the meanings given above, with a compound of the general formula

$$X-B_m \qquad (IV)$$

in which X represents a polymer; A and B being groups selected such that the compounds of (III) and (IV) will react together to give the desired compound of the formula (I).

The compounds of the general formula II have a number of applications. They may for example be used for direct clinical application to a patient, and accordingly, the present invention further provides a pharmaceutical composition comprising a novel compound of the general formula II together with a pharmaceutically acceptable carrier. The invention further provides a novel compound of the general formula II for use in therapy, and a method of treating a patient which comprises administering a pharmaceutically-effective amount of a novel compound of the formula II or a pharmaceutical composition according to the invention to the patient. Any desired pharmaceutical effect, for example trauma treatment, enzyme replacement, protein replacement, wound management, toxin removal, anti-inflammatory, anti-infective, immunomodulatory, vaccination or anti-cancer, may be obtained by suitable choice of biological molecule. Compounds of the general formula II may include an imaging agent; for example a radio-nucleotide, to enable tracking of the compound in vivo.

The compounds of the general formula II may also be used in non-clinical applications. For example, many physiologically active compounds such as enzymes are able to catalyse reactions in organic solvents, and compounds of the general formula II may be used in such applications. Further, compounds of the general formula II may be used as diagnostic tools.

Figure 2:
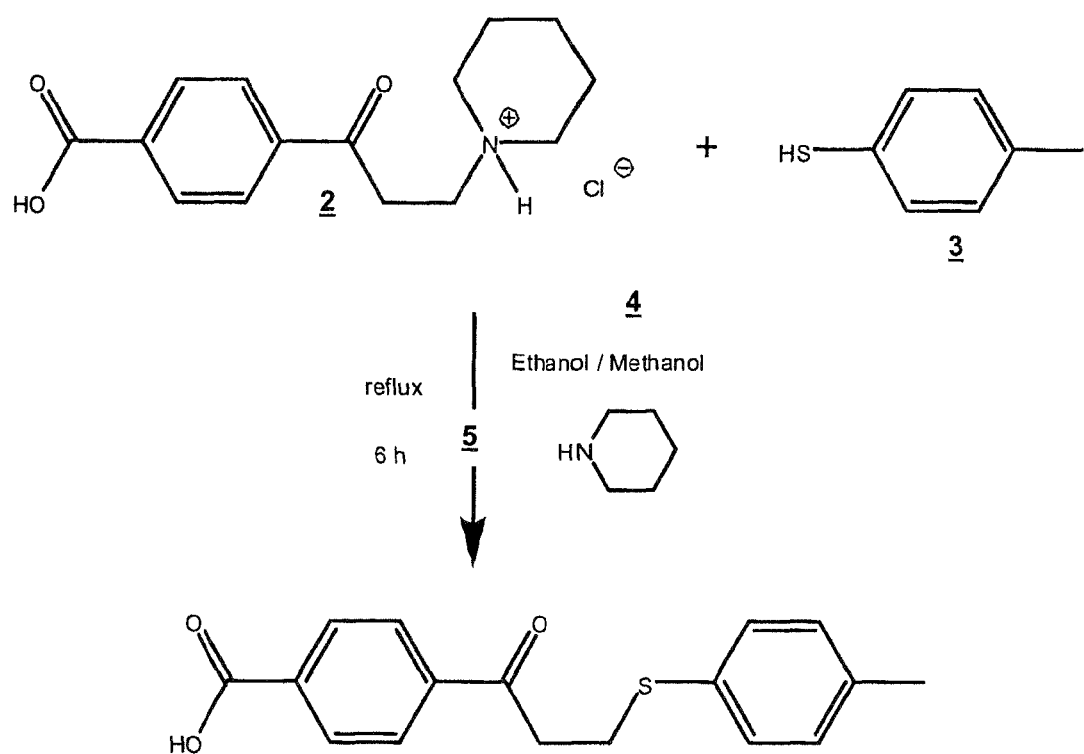
Figure 3:
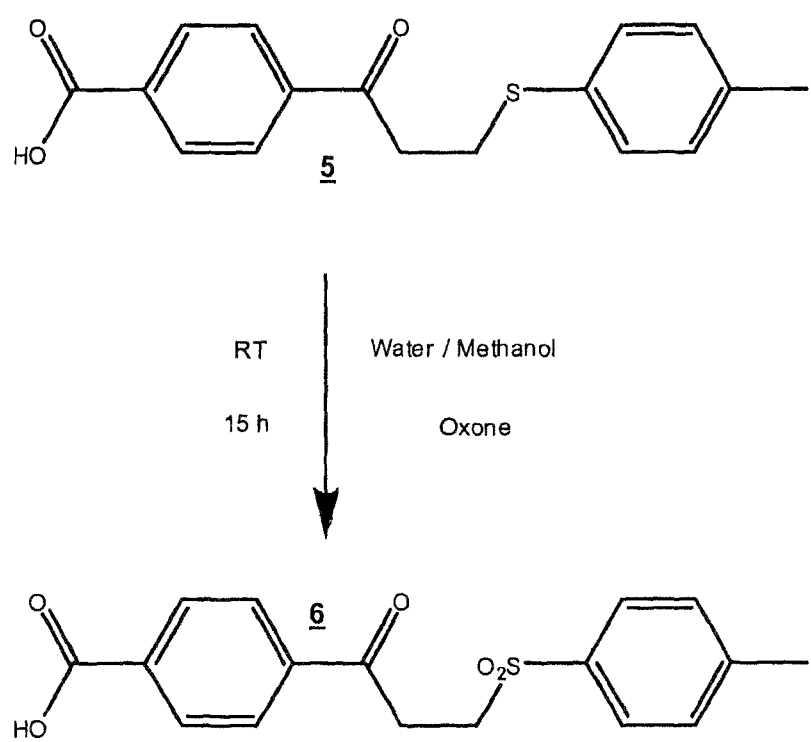
Figure 4:
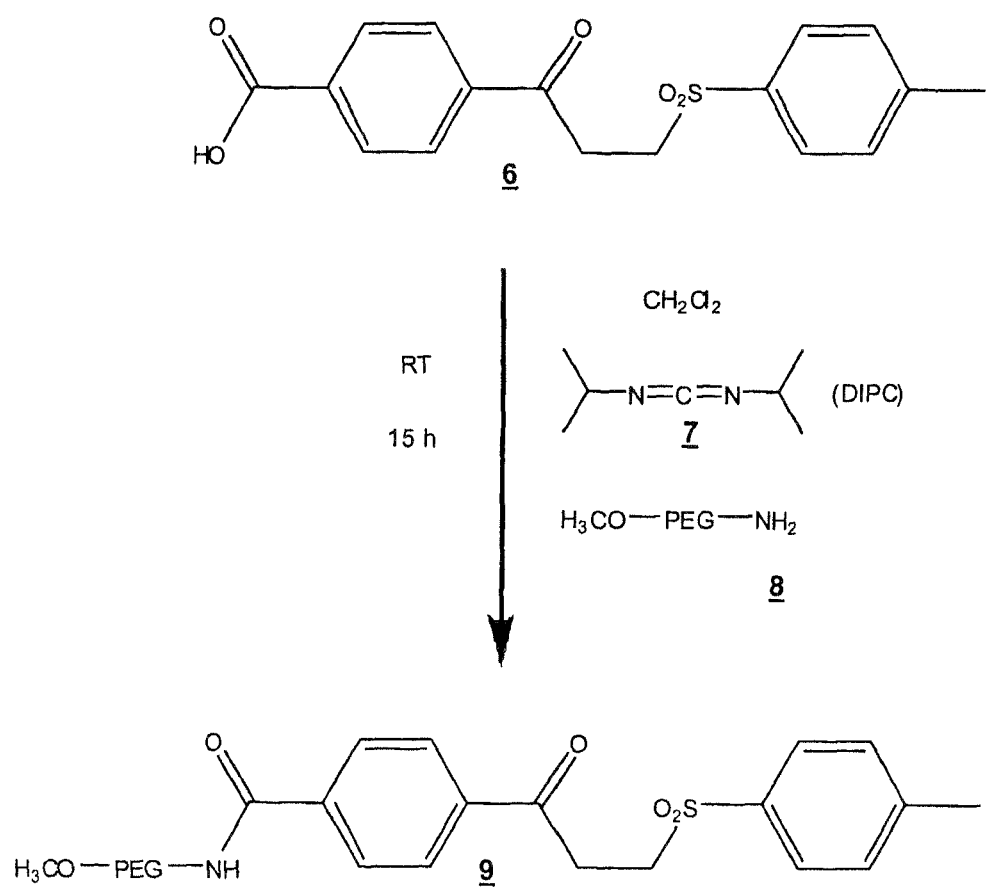
Figure 5:
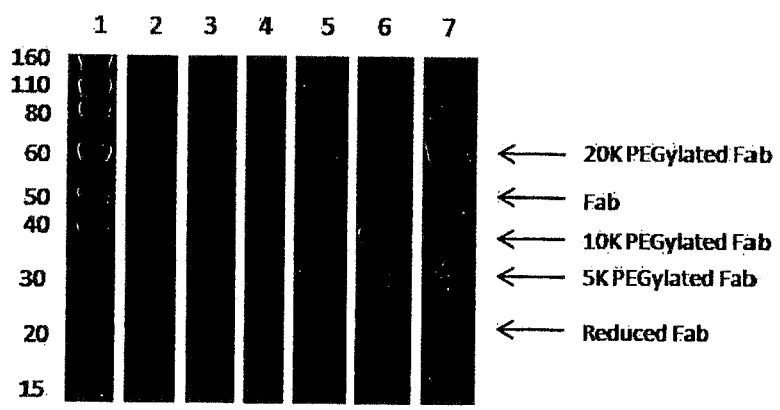
Figure 6:
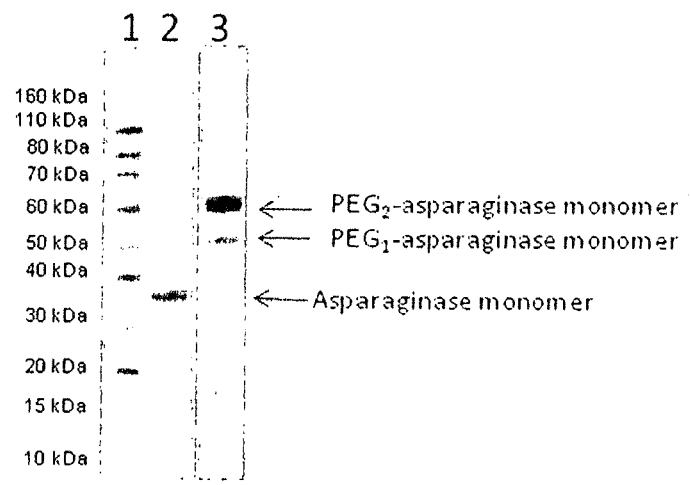
Figure 7:
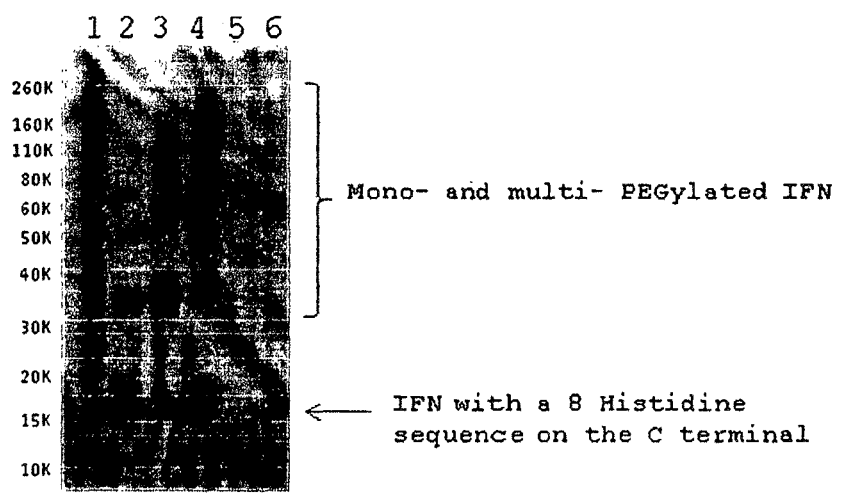
Figure 8:
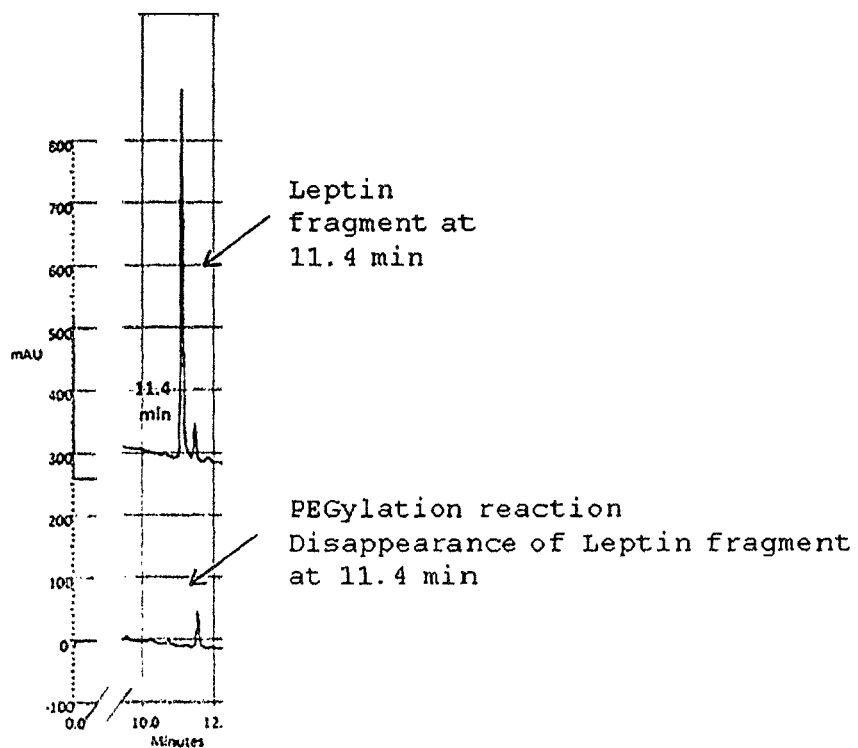
Figure 9:
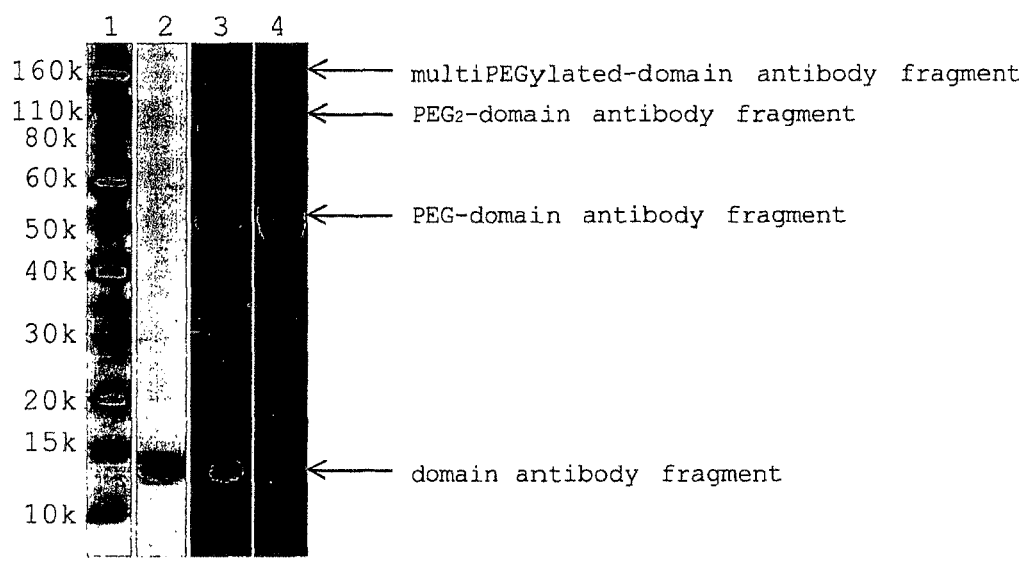
Figure 10:
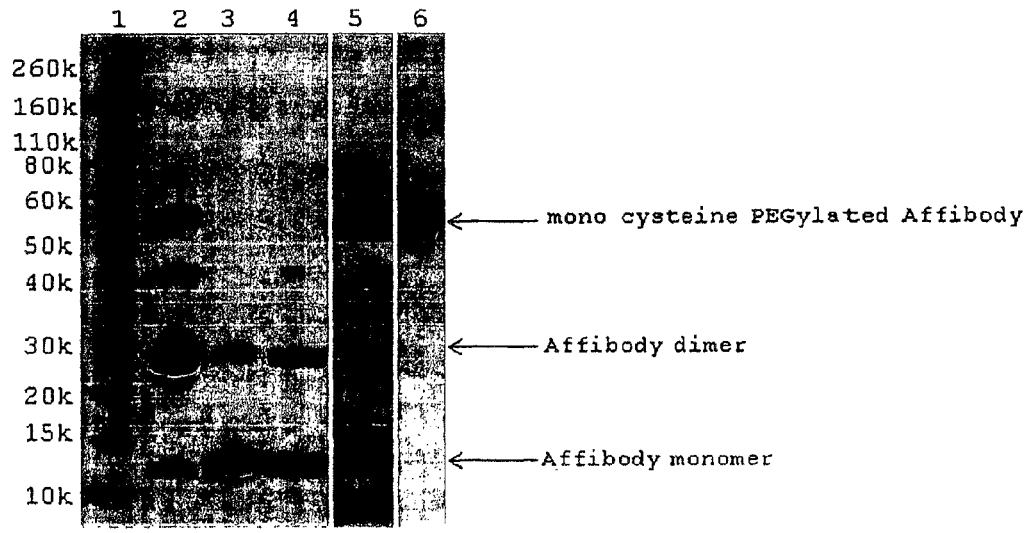
Figure 11:
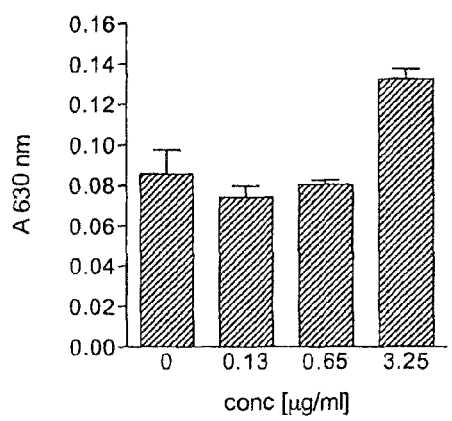
Figure 12:
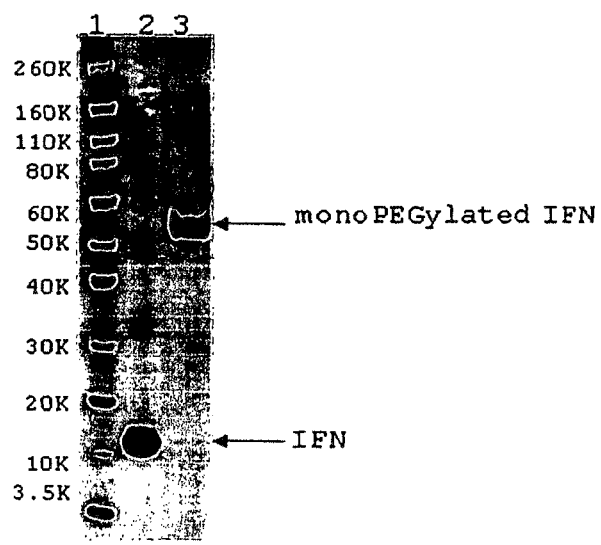
Figure 13:
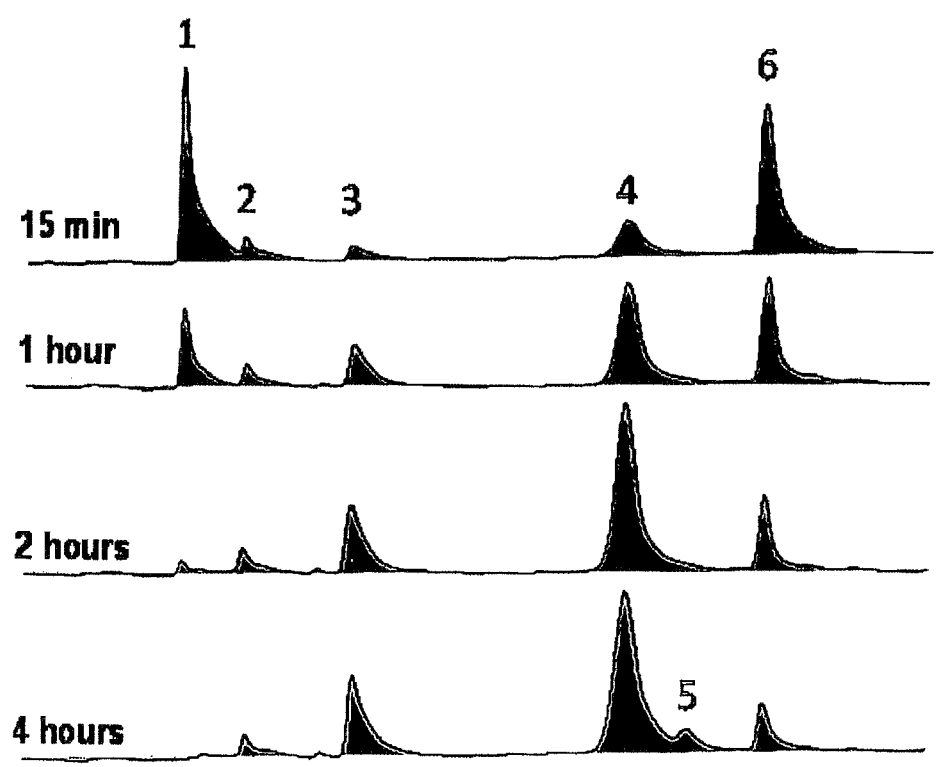
Figure 14:
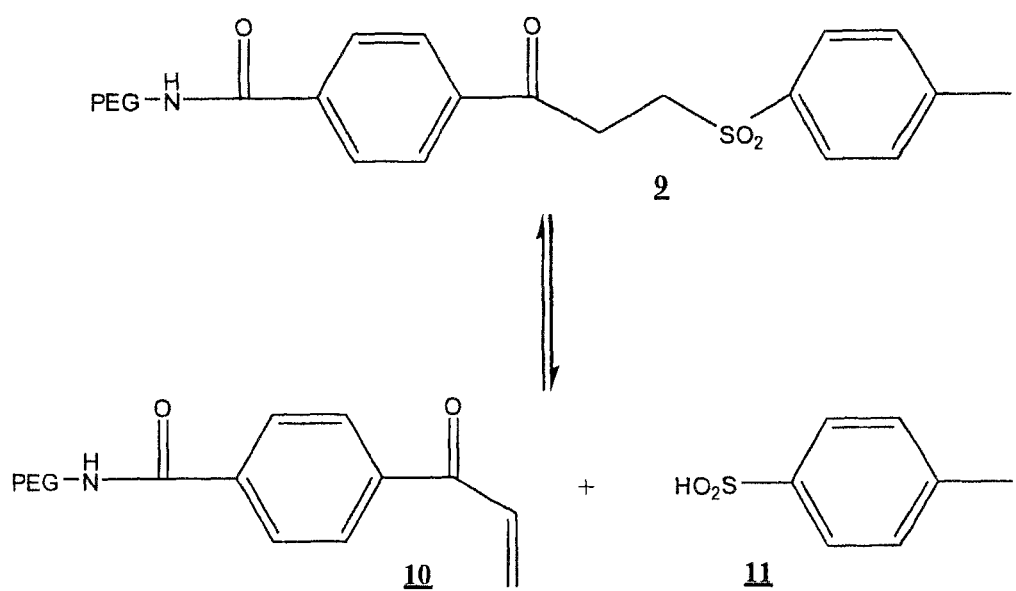
Figure 15:
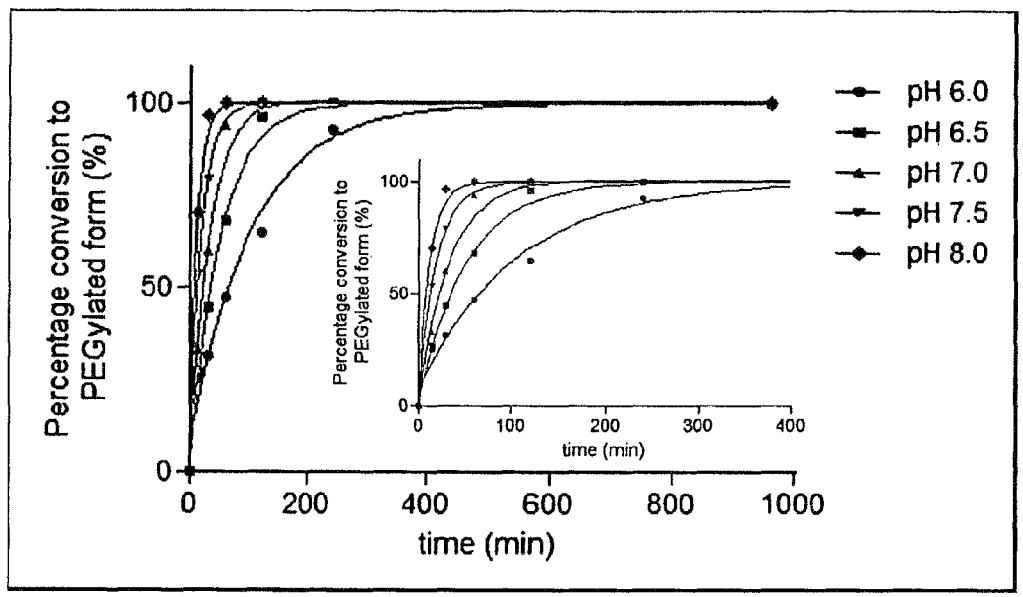
Figure 16:
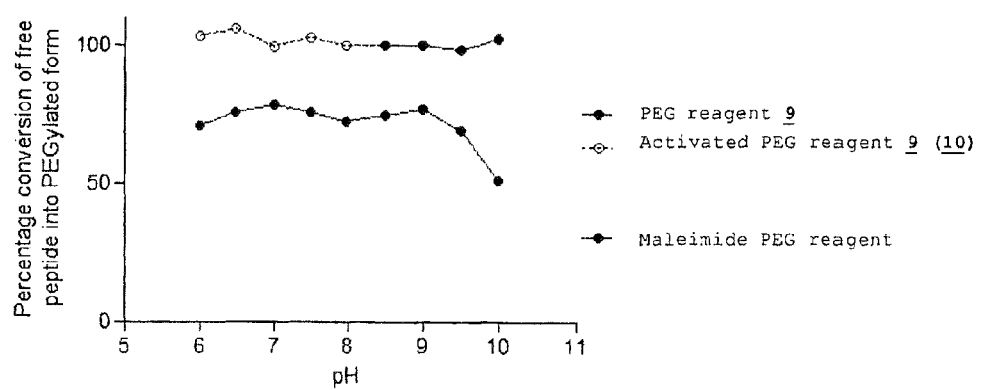
Figure 17:
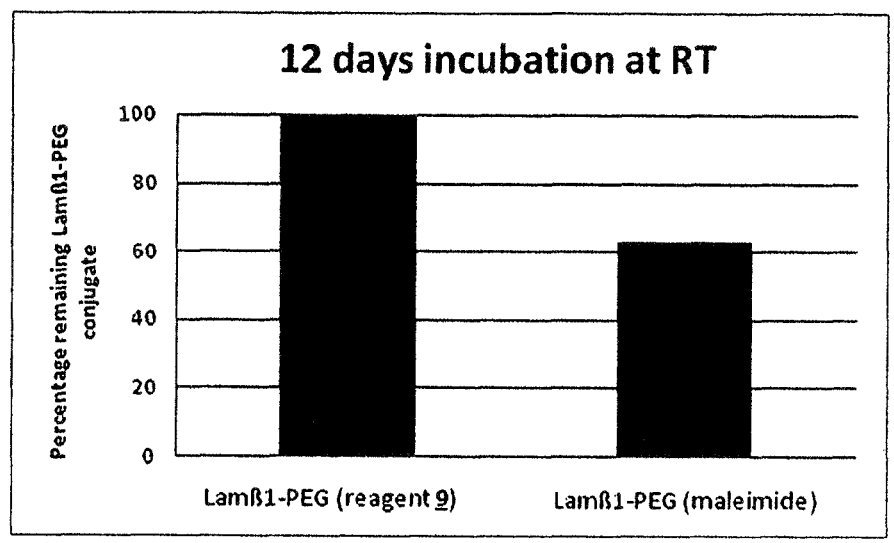
Figure 18:
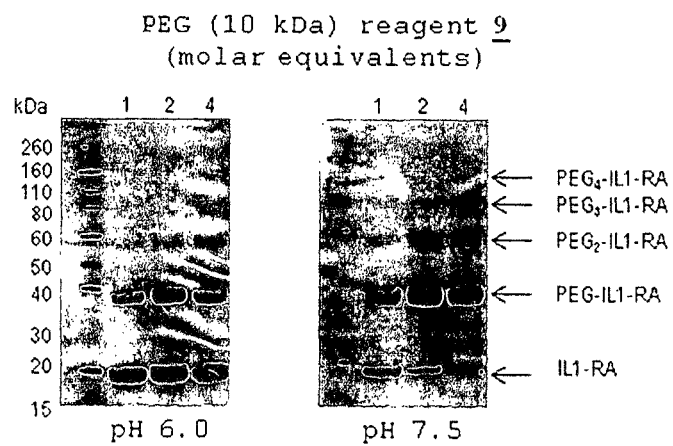
Figure 19:
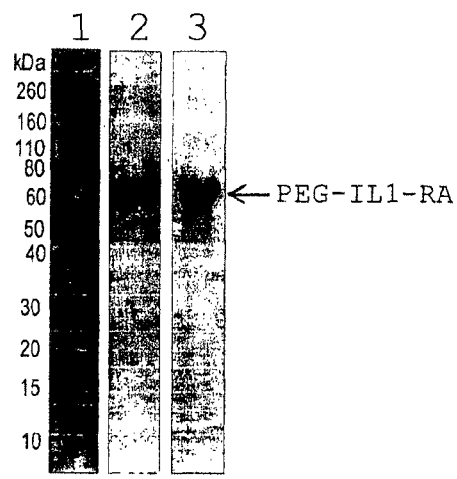
Figure 20:
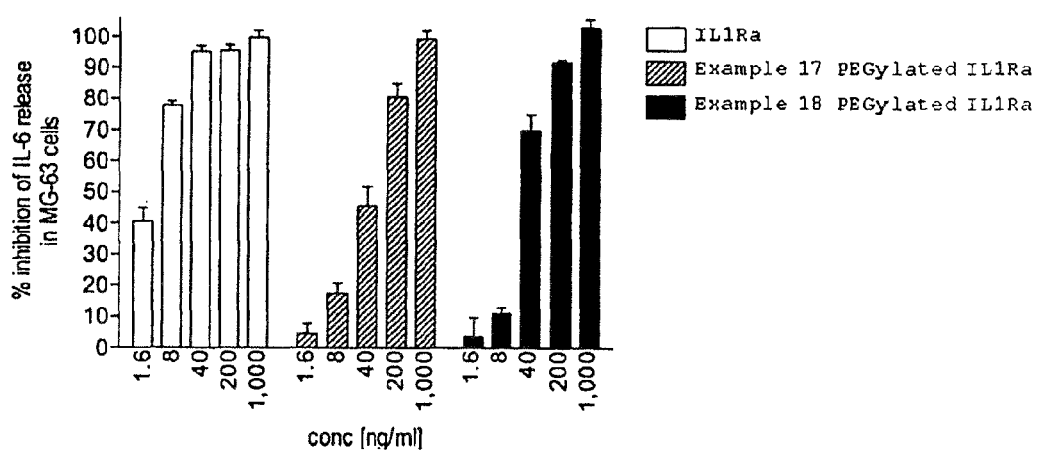
Figure 21:
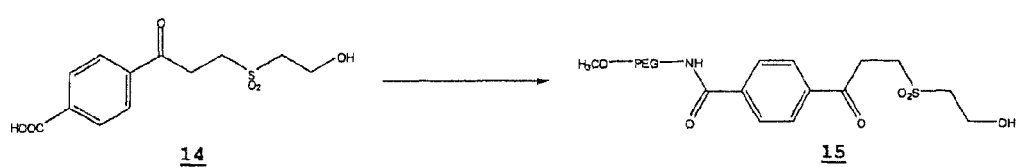
Figure 22:
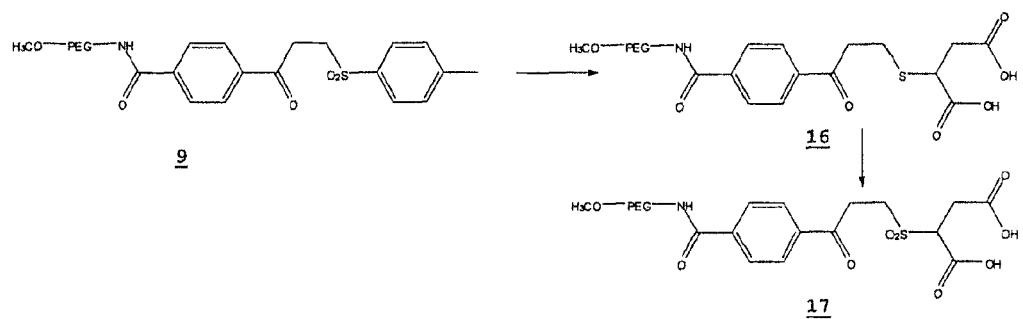

The following Examples illustrate the invention. In the accompanying drawings:

FIG. 1 shows the reaction scheme of step 1 of Example 1.
FIG. 2 shows the reaction scheme of step 2 of Example 1.
FIG. 3 shows the reaction scheme of step 3 of Example 1.
FIG. 4 shows the reaction scheme of step 4 of Example 1.
FIG. 5 shows the result of an SDS-PAGE analysis of the product of Example 2.
FIG. 6 shows the result of an SDS-PAGE analysis of the product of Example 3.
FIG. 7 shows the result of an SDS-PAGE analysis of the product of Example 5.
FIG. 8 shows reverse-phase chromatography analysis from the reaction in Example 6.
FIG. 9 shows the result of an SDS-PAGE analysis of the product of Example 7.
FIG. 10 shows the cation exchange chromatography analysis from the reaction in Example 8.
FIG. 11 shows the ELISA result of Example 8.
FIG. 12 shows the result of an SDS-PAGE analysis of the product of Example 9.
FIG. 13 shows chromatograms of the time-course PEGylation of Example 11.
FIG. 14 shows the interconversion of compounds 9, 10 and 11 as referred to in Examples 10 and 11.
FIG. 15 shows the conversion results of Example 11.
FIG. 16 shows the reverse-phase chromatography result of Example 12.
FIG. 17 shows the stability results of Example 13.
FIG. 18 shows the result of an SDS-PAGE analysis of the intermediate product of Example 17.
FIG. 19 shows the result of an SDS-PAGE analysis of the final product of Example 17.
FIG. 20 shows the absorbance results of Example 17.
FIG. 21 shows the reaction scheme of Example 19.
FIG. 22 shows the reaction scheme of Example 20.

EXAMPLE 1

PEG Reagent Synthesis: Synthesis of 10 kDa PEG Reagent 9

Step 1, Synthesis of p-carboxy-3-piperidinopropriophenone hydrochloride 2

The reaction scheme for this step is shown in FIG. 1.

A 250 ml round bottom flask was, charged with p-acetylbenzoic acid (15.0 g, 1), 11.11 g piperidine hydrochloride and 8.23 g paraformaldehyde. Absolute ethanol (90 ml) and concentrated hydrochloric acid (1 ml) were then added, and the resulting suspension heated under reflux for 10 h while stirring under argon. After stopping the reflux, acetone (150 ml) was added and the reaction mixture allowed to cool to room temperature. The resulting white precipitate was isolated on a glass filter (G3) and washed twice with chilled acetone. The solid was then dried under vacuum to give a white crystal powder (2, 9.72 g). $^1$H NMR (400 MHz, DMSO-$d_6$) δ 1.79, 2.96, 3.45 (br m, $CH_2$ of piperidine moiety), 3.36 (t, 2H, $COCH_2$), 3.74 (t, 2H, $NCH_2$), 8.09 (m, 4H, ArH).

Step 2: Synthesis of 4-(3-(p-tolylthio)propanoyl)benzoic acid 5

The reaction scheme for, this step is shown in FIG. 2.
The p-carboxy-3-piperidinopropriophenone hydrochloride 2 (1.0 g) and 4-methylbenzenethiol (417 mg, 3) were suspended in a mixture of absolute ethanol (7.5 ml) and methanol (5 ml). Piperidine (50 μl) was then added and the suspension heated to reflux with stirring for 6 h in an argon atmosphere. The white precipitate afforded after cooling to room temperature was filtered off with a glass filter (G3), washed carefully with cold acetone and dried in vacuum to give 5 (614 mg). $^1$H NMR (400 MHz, DMSO-$d_6$) δ 2.27 (s, 3H, phenyl-$CH_3$), 3.24, 3.39 (t, 2×2H, $CH_2$), 7.14, 7.26 (d, 2×2H, ArH of tolyl moiety), 8.03 (m, 4H, ArH of carboxylic acid moiety).

Step 3, Synthesis of 4-(3-tosylpropanoyl)benzoic acid 6

The reaction scheme for this step is shown in FIG. 3.
4-(3-(p-tolylthio)propanoyl)benzoic acid 5 (160 mg) was suspended in a mixture of water (10 ml) and methanol (10 ml). After cooling in an ice bath, oxone (720 mg, Aldrich) was added and the reaction mixture allowed to warm to room temperature while stirring overnight (15 h). The resulting suspension was diluted with further water (40 ml) so that it became nearly homogeneous and the mixture was then extracted three times with chloroform (in total 100 ml). The pooled chloroform extracts were washed with brine and then dried with $MgSO_4$. Evaporation of volatiles under vacuum at 30° C. afforded a white solid 6 (149 mg). $^1$H NMR (400 MHz, DMSO-$d_6$) δ 2.41 (s, 3H, phenyl-$CH_3$), 3.42 (t, 2H, CO—$CH_2$), 3.64 (t, 2H, $SO_2$—$CH_2$), 7.46, 7.82 (d, 2×2H, ArH of tolyl moiety), 8.03 (m, 4H, ArH of carboxylic acid moiety).

Step 4, Synthesis of PEGylated 4-(3-tosylpropanoyl)benzoic acid, PEG reagent 9

The reaction scheme for this step is shown in FIG. 4.
The 4-(3-tosylpropanoyl)benzoic acid 6 (133 mg) and O-(2-aminoethyl)-O'-methyl-PEG 8 (MW 10 kDa, 502 mg, BioVectra) were dissolved in dry toluene (5 ml). The solvent was removed under vacuum without heating and the dry solid residue was then redissolved in dry dichloromethane (15 ml) under argon. To the resulting solution, cooled in an ice bath, was slowly added diisopropylcarbodiimide (DIPC, 60 mg) under argon. The reaction mixture was then kept stirring at room temperature overnight (15 h). Volatiles were then removed under vacuum (30° C., water bath) to afford a solid residue that was redissolved with gentle heating (35° C.) in acetone (20 ml). The solution was filtered over non-absorbent cotton wool to remove insoluble material. The solution was then cooled in a dry ice bath to give a white precipitate that was separated by centrifugation (4600 rpm, 30 min). The liquid phase was decanted off and this precipitation procedure was repeated three times. Afterwards the resulting off-white solid was dried under vacuum to afford the PEG reagent 9 (437 mg). $^1$H NMR (400 MHz, $CDCl_3$) δ 2.46 (s, 3H, phenyl-$CH_3$), 3.38 (s, 3H, PEG-$OCH_3$), 3.44-3.82 (br m, PEG), 7.38, 7.83 (d, 2×2H, ArH of tolyl moiety), 7.95 (m, 4H, ArH of carboxylic acid moiety).

Analogous PEG reagents of different PEG molecular weights were prepared by the same general procedure. Thus, 20 kDa PEG was prepared by reaction of the sulfone 6 (20.8 mg), O-(2-aminoethyl)-O'-methyl-PEG (20 kDa, 250 mg, Fluka) and DIPC (8.7 mg, 7) in dry dichloromethane (15 ml) affording after the acetone precipitation purification procedure an off-white solid (245 mg). $^1$H NMR (400 MHz, $CDCl_3$) δ 2.46 (s, 3H, phenyl-$CH_3$), 3.38 (s, 3H, PEG-$OCH_3$), 3.44-3.82 (br m, PEG), 7.38, 7.83 (d, 2×2H, ArH of tolyl moiety), 7.95 (m, 4H, ArH of carboxylic acid moiety).

EXAMPLE 2

PEGylation of a Fab Antibody Fragment Possessing a Single Hinge Disulfide (Two Thiols) with PEG Reagents 9 of Molecular Weight 5, 10 and 20 kDa To 100 μl of a Fab solution (Abcam cat. no. AB6520, 1 mg/ml) was added 5 μl of a DTT stock solution (100 mM in deionised water) and the resulting solution allowed to stand at room temperature for 30 min. The solution was diluted to 200 μl with 95 μl of pH 7.8, 50 mM phosphate buffer with 0.15M NaCl and 10 mM EDTA, and then loaded on an illustra NAP-5 column (GE Healthcare cat. No. 17-0854-01), pre-equilibrated with pH 7.8, 50 mM phosphate buffer with 0.15M NaCl and 10 mM EDTA. The NAP-5 column was eluted with 5×300 μl of fresh pH 7.8 phosphate buffer. The UV absorbance at 280 nm was measured for all the fractions whereupon reduced Fab was identified to be mainly in fraction 3 and the protein concentration estimated to be 0.23 mg/ml.

Three PEG reagents with molecular weights 5 kDa, 10 kDa and 20 kDa were dissolved in pH 7.8 phosphate buffer to give 0.5 mg/ml, 1 mg/ml and 2 mg/ml solution concentrations respectively.

For each PEGylation reaction, 5.0 μl of the reduced Fab solution (0.23 mg/ml) and 0.42 μl of PEG solution (1 molar equivalent to reduced hinge disulfide thiols) was used. The Fab reaction solutions were also diluted with 4.6 μl of pH 7.8 phosphate buffer to give a final volume of 10 μl. The reaction solutions were incubated at 4° C. for 12 h.

SDS-PAGE analysis was then carried out on the reaction solutions using NuPAGE® Novex 4-12% Bis-Tris gels Invitrogen cat. No. NP0321BOX) and NuPAGE MES SDS running buffer (Invitrogen cat. No. NP002). The gels were stained with InstantBlue (Expedeon cat. No. ISB1L). FIG. 5 below shows the result. PEG on SDS-PAGE analysis runs approximately double its true size against protein markers, so a 5 kDa PEG runs like a 10 kDa protein. Fab is a protein of approximately 50 kDa and on a SDS-PAGE gel runs either as a single band at about 50 kDa when non-reduced or as a band or two bands at around 25 kDa for the reduced form. These are the heavy and light chains which are no longer held together by the hinge disulfide upon reduction and incubation with SDS. Therefore, although the Fab can be di-PEGylated whereby a single PEG is attached to each of the two cysteines of the reduced hinge disulfide in solution, SDS-PAGE analysis shows mono-PEGylation of the 25 kDa heavy and the light chains. In the lane labelled 1 are the protein markers (Novex sharp protein standards, Invitrogen cat. No. LC5800). Lane 2 shows Fab itself. The lane labelled 4 shows Fab reduced with DTT (around 25 kDa). Lane 5 shows the 5 kDa PEGylation result with the primary product a band at 35 kDa corresponding to PEGylated Fab. Only a small amount of reduced Fab remains at 25 kDa showing the Fab was mostly PEGylated. Lane 6 shows the 10 kDa PEGylation result with the primary product a band above the 40 kDa marker corresponding to 10 kDa PEGylated Fab. Lane 7 shows the 20 kDa result with the primary product a band above the 60 kDa marker corresponding to 20 kDa PEGylated Fab. Lane 3 shows the result of an attempted PEGylation without a previous reduction step: the fact that there is no PEGylated product indicates that the reaction site for PEGylation is a reduced disulfide bond.

EXAMPLE 3

PEGylation of Asparaginase with 5 kDa PEG Reagent

To 1 ml of a 1 mg/ml solution of asparaginase (Sigma cat. no A3809) in 20 mM sodium phosphate buffer containing 150 mM NaCl and 5 mM EDTA at pH 7.8, was added DTT (15.4 mg) and after vortexing for several seconds the resulting solution was left at room temperature for 40 min. The 1 ml of solution was then added to a PD-10 column (GE Healthcare cat. No. 17-0851-01) pre-equilibrated with pH 7.8 20 mM sodium phosphate buffer, containing 150 mM NaCl and 5 mM EDTA, collecting the eluent as the load fraction. The column was then eluted with 5×1 ml of fresh phosphate buffer. Fractions 3 and 4 were combined to give 2 ml.

A 10 mg/ml solution of 5 kDa PEG reagent 9 was, prepared in deionised water and 2.0 μl (1.5 equivalents of PEG to free thiols) was added to 100 μl of the reduced asparaginase. The solution was vortexed for several seconds and then placed at 4° C. overnight, whereafter a sample was taken for SDS-PAGE analysis. The result is shown in FIG. 6. Lane 1 shows the protein markers used to estimate MW, lane 2 shows asparaginase before PEGylation and lane 3 shows the reaction solution of reduced asparaginase with 5 kDa PEG reagent. A strong band corresponding to the PEGylation of both cysteines is seen as the primary product just above the 60 kDa protein marker. A second lower MW band is present just above the 50 kDa protein marker which corresponds to PEGylation of only one of the two cysteines. There is only a very faint band corresponding to reduced asparaginase between the 30 and 40 kDa protein markers showing that nearly all of the protein had PEGylated with PEG reagent 9.

EXAMPLE 4

PEGylation of G-CSF (Granulocyte-Colony Stimulating Factor) Possessing a Free Single Cysteine with PEG Reagent 9 with Molecular Weights of 5, 10 and 20 kDa and Comparison with a 5 kDa PEG Possessing a Maleimide Functional Group A GCSF stock solution (0.66 mg/ml in 50 mM sodium phosphate buffer, pH 6.2, with 150 mM NaCl and 10 mM EDTA) was divided into 5 fractions of 100 μL each (Native G-CSF and four fractions for the PEGylation reactions). The fractions were incubated overnight at 4° C. with 1 molar equivalent of PEG reagent to G-CSF. For 5 kDa PEG reagent 9 and for 5 kDa PEG maleimide (Fluka cat. no. 63187), this involved adding 3.5 μl of a 5 mg/ml PEG solution in deionised water. For 10 kDa PEG reagent 9 this involved adding 7 μl of a 5 mg/ml PEG solution in deionised water. For 20 kDa PEG reagent 9 this involved adding 14.0 μl of a 5 mg/ml solution in deionised water. The PEGylation reactions were analysed by SDS-PAGE (NuPAGE® Novex 4-12% Bis-Tris gels, MES buffer, all from Invitrogen, and Instant-Blue stain (Expedeon cat. No. ISB1L). G-CSF without PEG reagent added showed as a band between the 15 and 20 kDa protein markers. For the 5 kDa PEGylation with 9 a band at around 30 kDa corresponding to 5 kDa monoPEGylated GCSF was visible. For the 10 kDa PEGylation with 9 a band below 40 kDa was visible corresponding to 10 kDa monoPEGylated G-CSF. For the 20 kDa PEG result a band between 50 and 60 kDa corresponding to 20 kDa monoPEGylated G-CSF was visible. For the 5 kDa PEG maleimide reaction no band was seen other than unreacted G-CSF, showing that no reaction had occurred with this reagent.

EXAMPLE 5

PEGylation on Histidine in IFN α-2b with an 8 Histidine Sequence on its C Terminal with 10 kDa and 20 kDa PEG Reagent 9

To a 20 µl solution of IFN α-2b (1.13 mg/ml in 10 mM sodium phosphate buffer containing 2 mM EDTA and 150 mM NaCl, pH 7.5) was added 1 molar equivalent of 10 kDa PEG reagent 9 (1.8 µl of a 6 mg/ml solution in deionised water) and the resulting solution incubated overnight at room temperature. A repeat was also performed with 1 molar equivalent of 20 kDa PEG reagent 9 (3.3 µl of a 6.6 mg/ml solution in deionised water. Both samples were then analysed by SDS-PAGE (NuPAGE® Novex 4-120 Bis-Tris gels, MES running buffer, all from Invitrogen, and InstantBlue stain (Expedeon cat. No. ISB1L)). The result is shown in FIG. 7. In the lane labelled 1 are the protein markers. Lane 2 is the starting IFN only. Lane 3 shows the result of the 10 kDa PEG reagent 9 reaction. There are 5 distinct bands between the 30 and 160 kDa protein markers corresponding to IFN with 1 to 5 PEG chains conjugated. Lane 4 shows the result of the 20 kDa PEG reagent 9 reaction. There are three distinct bands between the 60 to 110 kDa protein markers corresponding to IFN with 1 to 3 PEG chains conjugated. The lane labelled 5 is the 20 kDa PEG reagent which does not stain, so no band is visible. The lane labelled 6 is the 10 kDa PEG reagent which does not stain, so no band is visible.

EXAMPLE 6

PEGylation of a Peptide (Leptin Fragment, with a Single Free Cysteine in the Structure) with 5 kDa PEG Reagent 9

Leptin fragment 116-130 amide mouse (Sigma cat. no. L6788) 1 mg was dissolved in 1 ml of 50 mM sodium phosphate buffer containing 150 mM NaCl and 10 mM EDTA at pH 7.8. A 5 mg/ml solution of 5 kDa PEG reagent 9 was prepared in the same buffer at pH 7.8. To a 50 µl of the leptin fragment solution was added 50 µl buffer and 96.1 µl of the PEG solution (3 molar equivalents of PEG to free thiol on cysteine). The solution was vortexed for several seconds and then placed at 4° C. overnight, whereafter samples were taken for RP-HPLC analysis. The RP-HPLC consisted of an analytical column Source 5RPC 4.6/150 (Amersham bioscience cat. no. 17511601) attached to a JASCO HPLC system. Buffer A was water+0.05% trifluoroacetic acid (Fisher scientific HPLC grade) and buffer B was acetonitrile (Fisher scientific HPLC grade). The method was 100% to 0% of buffer A over 30 minutes with a flow rate of 1 ml/min. The HPLC profile was monitored under 214 nm and 280 nm. Results for the leptin fragment, PEG reagent and the reaction solution are shown in FIG. 8.

The leptin fragment had a retention time of 11.4 min. In the reaction mixture this peak disappeared and was replaced with a peak at 16.5 min, showing that the fragment had successfully been derivatised.

EXAMPLE 7

PEGylation and Biological Activity of a Polyhistidine Tagged Domain Antibody Fragment with PEG Reagent 9 of Molecular Weight 20 kDa To 2.7 ml of an anti-TNF alpha domain antibody fragment solution (protein sequence taken from patent WO 2005/ 035572 as the sequence listed as TAR1-5-19 in FIG. 12 and expressed with a six-histidine tag on the C-terminus of the protein, 1.5 mg/ml in 50 mM sodium phosphate, 150 mM sodium chloride and 350 mM imidazole, pH 7.5) was added 0.3 ml of a solution of PEG reagent in deionised water (40 mg/ml, 1.9 molar equivalents to protein). The solution was transferred into D-Tube™ dialyzer (Novagen, cat. No. 71508-3) and dialysed against 1 L pH 6.2 buffer (50 mM sodium phosphate, 150 mM sodium chloride, 20 mM EDTA) at 4° C. over 16 h. The reaction solution was purified on a Resource S column (GE Healthcare, cat. No. 17-1178-01) using a linear gradient over 30 min from 20 mM sodium acetate, pH 4.5, to 20 mM sodium acetate with 700 mM sodium chloride, pH 4.5.

Fractions were collected and analysed using SDS-PAGE and the result is shown in FIG. 9. NuPAGE® Novex 4-12% Bis-Tris gels Invitrogen cat. No. NP0321BOX) and NuPAGE MES SDS running buffer (Invitrogen cat. No. NP002) were used and the gels were stained with InstantBlue (Expedeon cat. No. ISB1L). PEG on SDS-PAGE analysis runs approximately double its true size against protein markers, so a 20 kDa PEG runs like a 40 kDa protein. The domain antibody fragment is a protein of approximately 12.7 kDa. In the lane labelled 1 are the protein markers (Novex sharp protein standards, Invitrogen cat. No. LC5800). Lane 2 shows the protein only. The lane labelled 3 is the reaction solution. A band at 53 kDa corresponds to monoPEGylated protein. DiPEG-protein is represented by a band about 80 kDa and there is trace amount of multiPEGylated protein at the top of the lane. Lane 4 shows the purified monoPEGylated domain antibody fragment as a single band with no contamination from unPEGylated protein.

EXAMPLE 8

PEGylation and ELISA Binding of an Anti-TNF Alpha Affibody (1 Free Thiol Cysteine) with 20 kDa PEG Reagent 9

To 1 ml of a 1 mg/ml solution of anti-TNF alpha Affibody (Affibody AB cat. no 10.0841.01) in 50 mM sodium phosphate buffer containing 150 mM NaCl and 20 mM EDTA at pH 7.8, was added DTT (3.0 mg) to reduce any disulfide bonds and after vortexing for several seconds the resulting solution was left at room temperature for 30 min. The 1 ml of solution was then loaded to a PD-10 column (GE Healthcare cat. No. 17-0851-01) pre-equilibrated with pH 6.2 phosphate buffer (50 mM sodium phosphate, 150 mM NaCl and 20 mM EDTA). The column was then eluted with 5×1 ml of fresh pH 6.2 phosphate buffer. A280 nm measurements indicated fractions 3 and 4 contained the reduced protein and were combined to give 2 ml. To the protein solution was added 10 µl of a saturated aqueous hydroquinone solution and mixed well. A 20 mg/ml solution of 20 kDa PEG reagent 9 was prepared in deionised water and 73 µl (1 molar equivalent of PEG to free cysteine thiol) was added to the DTT treated affibody. The solution was vortexed for several seconds and then placed at ambient temperature for 3 h, whereafter a sample was taken for SDS-PAGE analysis.

After the 3 h, a significant amount of PEGylated protein had already formed so the PEGylation reaction was purified without allowing the reaction to go to completion. Purification was achieved using a Resource S cation exchange chromatography column (GE Healthcare, cat. No. 17-1178-01) with a linear salt gradient (0-700 mM NaCl) over 30 min with pH 4.5, 20 mM sodium acetate mobile phase. The result is shown in FIG. 10. The lane labelled 1 in FIG. 10 shows the protein markers used to estimate MW. The lane labelled 2 shows the affibody solution before treatment with DTT. The affibody in the presence of DTT is shown in the lane labelled 3. Lane 4 shows the affibody after removal of the DTT by PD-10 column and two bands are visible corresponding to monomeric affibody (free thiol cysteine available for PEGylation) and dimeric affibody (cysteines not available for PEGylation). The lane labelled 5 shows the PEGylation reaction solution. A band just above the 50 kDa protein marker can be seen for the mono PEGylated affibody. The cation exchange chromatography purified monoPEGylated affibody is shown in lane 6 as a single band with no contamination from unPEGylated protein.

The Binding Activity of the Purified Mono PEGylated Product to TNF-α was Analysed by an ELISA Method:

TNF-α (10 ug/ml in 15 mM $Na_2CO_3$, 34.9 mM $NaHCO_3$, pH 9.6) was added to a 96-well microtitre plate (Maxisorp, Nunc) at 100 μl/well and incubated at 4° C. overnight. TNF-α was then removed and PBS/1% BSA was added at 100 μl/well and incubated for 1 h at RT. PBS/1% BSA was then removed and the PEGylated anti-TNF-α affibody (0.026, 0.13, 0.65, 3.25 ug/ml in PBS/1% BSA) added and incubated for 1 h at RT. No PEGylated affibody was added to the control wells. The plate was then washed three times with 300 μl/well of PBS/0.1% Tween 20 (PBS/T). Anti-PEG rabbit antibody (Epitomics, cat no. 2061-1; 1:1000 in 1% BSA/PBS) was then added at 100 μl/well and incubated for 1 h at RT. Following three washes with PBS/T, horseradish peroxidase-conjugated anti-rabbit antibody (Abcam, cat no. ab6721; 1:1000 in PBS/1% BSA) was added at 100 μl/well and incubated for 1 h at RT. Wells were then washed three times with PBS/T and 3,3',5,5'tetramethylbenzidine substrate (Sigma-Aldrich, cat no. T0440) was added at 100 μl/well. After 15 min incubation in the dark, stop reagent (Sigma-Aldrich, cat no. S5689) was added at 100 μl/well and the absorbance read at 650 nm.

The ELISA result, shown in FIG. 11 shows specific binding to TNF-α by the PEGylated affibody, confirming that the protein retains activity post-PEGylation. In the absence of TNF-α there was no binding of anti-PEG antibody.

EXAMPLE 9

PEGylation on a Histidine Sequence of Interferon Alpha-2b (IFN α-2b) Possessing an 8 Histidine Sequence on its N-Terminal Using 20 kDa PEG Reagent 9. The Anti-Viral Activity of the 20 kDa PEGylated IFN with and without Reduction with Sodium Borohydride To a 4.67 ml solution of IFN α-2b with a 8 histidine sequence on the N-terminal (1.07 mg/ml in 5.0 mM sodium phosphate buffer containing 150 mM NaCl, pH 7.4) was added 2.6 molar equivalents of 20 kDa PEG reagent 9 (217 μl of a 60 mg/ml solution in deionised water) and the resulting solution incubated overnight at room temperature. The reaction sample after analysis by SDS-PAGE (NuPAGE® Novex 4-12% Bis-Tris gels, MES running buffer, all from Invitrogen, and InstantBlue stain (Expedeon cat. No. ISB1L)) was subjected to high performance anion exchange chromatography (TOSOH DEAE column, STSKgel DEAE-5PW, Supelco Cat No. 8-07164, connected to a Jasco HPLC system) to purify the monoPEGylated IFN α-2b. The fractions obtained (1 ml each) from the ion exchange column were analysed by SDS-PAGE. The fractions containing predominantly monoPEGylated IFN were subjected to lyophilisation. The resultant residue obtained after lyophilisation was dissolved in 50 mM sodium phosphate buffer containing 150 mM NaCl and 2 mM sodium borohydride and left still at room temperature for 1 h. The resultant solution was then subjected to size exclusion chromatography (HiLoad 16/60, Superdex 200, 50 mM PBS as eluent, 1.6 ml/min flow rate and detection at 214 nm) to isolate the monoPEGylated IFN. The sample isolated was analysed by SDS-PAGE and the result is shown in FIG. 12. In the lane labelled 1 of FIG. 12 are the protein markers. The lane labelled 2 shows the starting IFN only. Lane 3 shows a single band between the 50 and 60 kDa protein markers corresponding to the purified 20 kDa monoPEGylated IFN α-2b.

Antiviral activity: Antiviral assay was performed on A549 cells cultured in DMEM/10% fetal calf serum (FCS) containing penicillin and streptomycin. A549 cells were resuspended in DMEM/10% FCS at a concentration of 0.2×106 cells/ml and aliquoted at 50 μl/well into 96-well microtitre plates. The next day, PEGylated and native IFN samples were prepared in a 2-fold dilution, and 50 μl of each dilution was added to the wells. The plates were then incubated for 24 h. The media was then removed and the cells were inoculated with encephalomyocarditis virus (EMCV) prepared in DMEM/5% FCS, (50 μl/well). Cells were incubated for further 24 h, then washed with 300 μl/well of PBS and stained with 4% formaldehyde/0.1% methyl violet (50 μl/well; Sigma-Aldrich, cat no. 198099) for 30 min. The plate was then washed twice with 300 μl/well of PBS and air-dried. The dye was solubilized with a 2% SDS solution (50 μl/well) and the absorbance was measured at 570 nm. The 20 kDa PEGylated IFN-α2b (A) untreated or (B) treated with sodium borohydride showed activity of 64 pg/ml and 68 pg/ml, respectively.

EXAMPLE 10

PEG Reagent 9 Stability Compared to Commercial PEG Reagents with Maleimide Functional Groups The stability of PEG reagent 9 (5 kDa and 20 kDa samples) was compared to methoxy poly(ethylene glycol) maleimidopropionamide (Chirotech Technology Ltd, cat. no. 008-008, lot no. 223126001) and α-methoxy-ω-ethyl-maleinimide polyethylene glycol (Iris Biotech cat. no. PEG1146, lot no. 128512) by nuclear magnetic resonance (NMR) spectroscopy at pH 7.4. A pH 7.4 $D_2O$ solution was made by first freeze-drying a 50 mM sodium phosphate aqueous solution containing 150 mM NaCl and 20 mM EDTA at pH 7.4 and reconstituting to the same volume with deuterium oxide. Acetone was added as a standard to the buffer at 1.0 μl per 3 ml. Samples of the PEG reagents were dissolved at 1 μmol in 0.75 ml of the buffer and analysed after 4 h and after 25.5 h by 400 MHz NMR spectroscopy. The stability of the PEG maleimide samples was determined by comparing the integral at 6.86 ppm after normalising using the integral for the acetone standard at 2.17 ppm. The stability of PEG reagent 9 was determined by comparing the total integral for the signals at 7.31, 7.40, 7.47, 7.73, and 8.03 ppm after normalising using the integral for the acetone standard at 2.21 ppm. The peaks at 7.31, 7.47 and 8.03 are from the protein active PEG reagent 10 (FIG. 14) formed as expected from PEG reagent 9. The ratio of 9 to 10 ranged from 1.46 to 1.77 to 1 for both sample 1 and 2 during the course of the experiment. The stability study results are shown in Table 1. The PEG maleimide samples degraded by between 19 and 55% over 21.5 h at pH 7.4 while the PEG reagent 9 samples did not degrade under the same conditions.

TABLE 1

Results for a NMR stability study comparing PEG reagent 9 with PEG maleimide.

| Sample | 4 h Integral for 6.86 ppm peak | 25.5 h Integral for 6.86 ppm peak | % Degradation over 21.5 h at pH 7.4 |
|---|---|---|---|
| PEG maleimide sample 1 | 1.16 | 0.52 | 55 |
| PEG maleimide sample 2 | 0.75 | 0.61 | 19 |

| Sample | 4 h Total Integral for 7.31, 7.40, 7.47, 7.73, 8.03 ppm peaks | 25.5 h Total Integral for 7.31, 7.40, 7.47, 7.73, 8.03 ppm peaks | % Degradation over 21.5 h at pH 7.4 |
|---|---|---|---|
| PEG reagent 9 sample 1 | 4.85 | 4.82 | <1 |
| PEG reagent 9 sample 2 | 3.93 | 4.01 | 0 |

EXAMPLE 11

PEGylation of Laminin Fragment 925-983 (Lamβ1$_{925-933}$) Containing a Single Free Cysteine Thiol at Varying pH Lamβ1$_{925-933}$ is a synthetic linear nonapeptide (Cys-Asp-Pro-Gly-Tyr-Ile-Gly-Ser-Arg-NH$_2$) (Sigma cat. no. C0668), which corresponds to residues 925-933 of the laminin B1 chain and contains a single cysteine thiol.

PEGylation with PEG Reagent 9 at Varying pH:

Lyophilised Lamβ1$_{925-933}$ peptide (1 mg) was dissolved into 500 µl of deionised water to give a 2 mg/ml stock solution. After vortexing, the peptide stock solution was used fresh or aliquoted and stored at −80 µC. until use. The Lamβ1$_{925-933}$ stock solution was diluted two-fold to give a final concentration of 1 mg/ml (1 mM) in the PEGylation reaction mixture. The 5 kDa PEG reagent 9 (5 mg) was dissolved into 200 µl of deionised water to give a 25 mg/ml stock solution. After vortexing, the PEG reagent stock solution was used fresh or aliquoted and stored at −80° C. until use. The PEG stock solution was diluted five-fold to give a final concentration of 5 mg/ml (1 mM) in the PEGylation reaction mixture. The buffer stock solution contained 1 M sodium phosphate buffer for the pH 6.0-8.0 range and 1 M sodium carbonate-bicarbonate buffer for the pH 8.5-10.0 range. For all pH values, the buffer stock solution also contained 10 mM EDTA and 381 µM hydroquinone. The buffer stock solution was diluted ten-fold to give a final concentration of 100 mM buffering agent (sodium phosphate or sodium carbonate-bicarbonate), 1 mM EDTA and 38 µM hydroquinone.

Each PEGylation reaction mixture contained 5 µl Lamβ1$_{925-933}$ stock solution, 1 µl buffer solution, 2 µl of PEG reagent solution (corresponding to a 1:1 molar ration of PEG reagent to Lamβ1$_{925-933}$ model peptide) and 2 µl of deionised water to give a total reaction volume of 10 µl. After vortexing for several seconds, followed by brief centrifugation (30 s at 5,000×g) to collect the solution at the bottom of the tube, the reaction mixtures were incubated standing at room temperature for 0.25, 0.5, 1, 2, 4, 16 and 24 hours. After incubation at room temperature, the tubes containing the reaction mixtures were placed at −80° C. and stored until analysis by reverse-phase chromatography.

For the reverse-phase chromatography assay a Source 5RPC ST 4.6/150 (GE Healthcare, cat. no. 17-5116-01) column was used. The column was connected to a Jasco HPLC system comprising a Jasco PU-980 Intelligent HPLC Pump, a Jasco LG-980-02 Ternary Gradient Unit, a Jasco Degassys Populaire Degassing Unit, a Jasco UV-970 4-λ Intelligent UV Detector, A Jasco LC-NetII/ADC Interface for connection to a PC and a Rheodyne 7725i manual injector valve. The HPLC system was controlled through a computer using the EZchrom SI version 3.2.1 Build 3.2.1.34 chromatography software package (Agilent Technologies). Chromatogram analysis and data export were also performed using the EZchrom SI chromatography data system.

A three-eluent system was used. Eluent A contained 5% acetonitrile (Far UV, HPLC grade, Fisher cat. no. A/0627/17) and 0.065% trifluoroacetic acid (TFA) (Acros cat. no. 139721000) in deionised water. Eluent B contained 0.075% TFA in acetonitrile, while Eluent C was 100% acetonitrile. Eluents were degassed by sonication before use. The elution program involved a 0-64% B gradient in 20 minutes, followed by wash in 100% acetonitrile and re-equilibration in eluent A (Table 2). A constant flow rate of 1 ml/min was maintained throughout the run. The absorbance at 215, 250, 280 and 350 nm was recorded throughout the run. Each sample (10 µl) was thawed and briefly centrifuged (1 min at 14,000 g) immediately before 5 µl of supernatant were injection into the reverse phase chromatography column.

TABLE 2

Settings for the gradient elution program used for the reverse phase chromatography assay

| Time (min) | Flow rate (ml · min$^{-1}$) | A (%) | B (%) | C (%) |
|---|---|---|---|---|
| initial | 1.00 | 100 | 0 | 0 |
| 20.00 | 1.00 | 36 | 64 | 0 |
| 20.20 | 1.00 | 0 | 0 | 100 |
| 24.00 | 1.00 | 0 | 0 | 100 |
| 24.20 | 1.00 | 100 | 0 | 0 |
| 30.00 | 1.00 | 100 | 0 | 0 |

The identity of each peak in the chromatograms was confirmed by running standard samples (PEG reagent, reduced and oxidised unreacted peptide) and by analytical size exclusion chromatography (SEC) for relative size estimation (for PEGylation product: peptide-PEG conjugate). The column used for analytical SEC was a BioSep-SEC-S3000 (300×7.8 mm) analytical column (Phenomenex, cat. no. 00H-2146-KO). The running eluent used was 10 mM sodium phosphate buffer (pH 7.0) containing 10% (v/v) acetonitrile and the flow rate was kept constant at 2 ml/min throughout the run.

FIG. 13 shows chromatograms of a time-course PEGylation experiment at pH 6.5, using 1 molar equivalent of 5 kDa PEG reagent 9. After 15 minutes incubation at room temperature, five peaks are visible: the PEG reactive peptide Lamβ1$_{925-933}$ (peak 1); an unreactive peptide dimer formed through disulfide formation (peak 2); the PEG reagent 9 sulfonic acid leaving group (peak 3, compound 11 in FIG. 14); a peak corresponding to PEGylated peptide product (5 kDa PEG-Lamβ1$_{925-933}$ conjugate) (peak 4) and the PEG reagent 9 (peak 6, unreactive form).

After 4 hours incubation, all the free peptide (peak 1) had been consumed as the PEGylation went to completion. Sortie excess activated PEG reagent peak (peak 5, compound 10 in FIG. 14) is also present because some of the peptide formed an unreactive dimer (peak 2, note that the PEG reagent absorbs more strongly than the peptide at equivalent concentrations). The oxidised Lamβ1$_{925-933}$ (peak 2) could not be PEGylated as it possesses no free thiol and hence its corresponding peak (peak 2) remained unchanged during the course of the experiment. This result is consistent with cysteine thiol PEGylation occurring for the reduced peptide.

The reactivity of PEG reagent 1 towards Lamβ1$_{925-933}$ between pH 6.0 and pH 8.0 was assessed by measuring the conversion of peptide (peak 1) to 5 kDa PEGylated Lamβ1$_{925-933}$ product (peak 4). The peptide peak results were normalised by assigning the value of 100 to the calibrated peak area corresponding to the total amount of peptide used in each PEGylation reaction, while the product peak results were normalised using a deduced maximal product peak area corresponding to total conversion of peptide into product. Conversion (%) was defined as the proportion of PEGylated peptide relative to the initial amount of peptide used in the reaction. The result is shown in FIG. 15. At pH 6.0, 6.5, 7.0, 7.5 and 8.0 all the peptide was PEGylated. The rate to go to completion depended on the pH, the higher the pH the faster the rate, and reflects the different rate of formation of the reactive structure 10 (FIG. 14) at different pH.

EXAMPLE 12

Comparison of the Reactivity of PEG Reagent 9 and a Commercially Available PEG Maleimide at Varying pH The reactivity of PEG reagent 9 towards the Lamβ1$_{925-933}$ peptide of Example 11, was compared to a commercially available thiol reactive PEG reagent, PEG maleimide (O-(2-maleimidoethyl)-Ω'-methyl-polyethylene glycol 5,000, Fluka cat. no. 63187). To ensure that PEG reagent 9 was immediately available for reaction in the experiment timescale, the reagent was first allowed to form the thiol reactive form (Reagent 10, FIG. 14) by incubating at pH 7.5 (2 hours, 4° C.) and the reagent 10 isolated by RP chromatography prior to peptide conjugation. All peptide reactions were carried out with freshly dissolved PEG reagent. Briefly, the PEGylation reaction solution (reaction scale 10 µl) contained 10 µg Lamβ1$_{925-933}$, 50 µg of PEG (5 kDa) reagent (corresponding to a 1:1 molar ratio of PEG reagent to Lamβ1$_{925-933}$ model peptide) in 100 mM sodium phosphate buffer (pH 6.0-8.0) or 100 mM sodium carbonate-bicarbonate (pH 8.5-10.0) and 1 mM EDTA. After incubation at room temperature, the reaction mixtures were analysed by reverse-phase chromatography as described previously in Example 11. The result is shown in FIG. 16. For PEG reagents 9 (pH 9.0 to 10) and 10 (pH 6.0 to 8.0), full conversion of the peptide to the PEGylated form could be achieved between pH 6.0 and pH 10 within 15 minutes.

For the PEG maleimide reagent conversion only reached a maximum of 78.9% after the 15 minutes. At higher pH, the conversion was even lower (51.2 at pH 10). The PEG maleimide reaction at pH 8.5 was sampled again after 16 h and all the peptide had been consumed.

At all pH values tested therefore, PEG reagents 9 and 10 were more efficient than the PEG maleimide reagent.

EXAMPLE 13

Stability of a PEG Reagent 9 Peptide Conjugate and Comparison with a PEG Maleimide Derived Peptide Conjugate The stability of purified Lamβ1$_{925-933}$ peptide conjugates made from PEG reagent 9 and PEG maleimide from Example 12 were compared over 12 days. The stability of the conjugates was determined by monitoring the area of the PEG-peptide peak using reverse phase chromatography as described in Example 11.

Synthesis of PEGylated Lamβ1$_{925-933}$ with PEG Reagent 9:

The conjugate was prepared using a modified method of Example 11. (pH 6.0 using a final peptide concentration of 1.6 mg/ml and 0.4 mg peptide). The product was isolated by RP-chromatography. The elution peak corresponding to the Lamβ1$_{925-933}$-PEG conjugate was collected, lyophilised and subsequently re-suspended in deionised water. Finally, 2 mM of sodium borohydride (Acros Organics, cat. no. 200050250) were added and after the sample was incubated for 30 minutes at room temperature, 50 mM of sodium phosphate buffer (pH 7.5) was added. Synthesis of PEGylated Lamβ1$_{925-931}$ with PEG maleimide: Lamβ1$_{925-933}$ (0.4 mg) was used for PEGylation with 5 kDa PEG maleimide (5 kDa, Fluka cat no. 63187) reagent. Briefly, 20 µl of 10× buffer stock solution (containing 1 M sodium phosphate buffer (pH 8.0) and 10 mM EDTA) and 40 µl of PEG reagent stock solution (25 mg/ml in deionised water) were added to 200 µl of peptide stock solution (2 mg/ml in deionised water). After 1.5 hours incubation at room temperature, the product was purified using as RP chromatography as described in Example 11. The elution peak sample was lyophilised and subsequently re-suspended in deionised water and then 50 mM of sodium phosphate buffer was added to adjust the pH to 8.0. RP chromatography was used to make sure the concentrations of both PEG-peptide solutions were approximately equal.

Both stability samples were incubated at room temperature. After 12 days, samples were analysed by analytical RPC and the stability determined by the change in the area of integration for the conjugate peaks as shown in FIG. 17. The conjugate derived from PEG reagent 9 remained stable over 12 days. For the conjugate derived from PEG maleimide, only 63% remained in the chromatogram showing that PEG reagent 9 lead to a more stable product.

EXAMPLE 14

PEGylation Using PEG Functionalised at Both Ends PEG Reagent 12

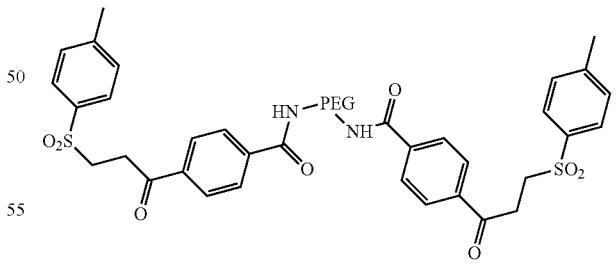

12

PEG reagent 12 was prepared in an analogous way to PEG reagent 9 using O,O'-bis(2-aminoethyl)polyethyleneglycol 6000 (Fluka cat. no. 14504) and allowed to react with the model peptide from Example 11 (Lamβ1$_{925-933}$). Water (6 µl), 2 µl of 10× buffer stock solution (containing 1 M sodium phosphate buffer (pH 8.0), 381 µM hydroquinone and 10 mM EDTA) and 2 µl PEG reagent 12 (25 mg/ml) reagent were added to 10 µl Lamβ1$_{925-933}$ stock solution (2 mg/ml in deionised water). This corresponded to a molar ratio of 1:0.375 model peptide to PEG reagent. The reaction solution (5 μl) was analysed by analytical RPC (as described in Example 11) after 2.5 h incubation at room temperature. All components of the reaction solution eluted as separate peaks: $Lam\beta1_{925-933}$ monomer eluted at 8.1 min, oxidised $Lam\beta1_{925-933}$ dimer eluted at 8.9 min, un-activated PEG reagent eluted at 17.3 min, activated PEG reagent eluted at 15.7 min and the leaving group 11 at 10.1 min. The product peak eluted at 14.2 minutes. After 2.5 h, 65% of the free $Lam\beta1_{925-933}$ present (86% reaction on reagent 12) in the reaction solution had been conjugated showing that both reactive ends of the PEG reagent 12 undergo reaction and that this bis-functional reagent can be successfully used to attach one peptide molecule at both ends of a PEG molecule.

EXAMPLE 15

Use of poly(1-vinyl-2-pyrrolidone) (PVP) as the Polymer Component: Conjugation of PVP with Lamβ1925-933 Model Peptide Preparation of PVP Reagent (3 Steps):
Step 1: PVP with a Terminal Amine Group:
A pressure tube was charged with cysteamine (0.028 g), dioxane (8 ml) and a magnetic stir bar. After gentle heating to allow a solution to form, the solution was purged with argon at room temperature for 5 min. While still purging, 1-vinyl-2-pyrrolidone (2.0 g) was then added and after a further 5 min this was followed by 2,2'-azobis(2-methylpropionitrile) (0.089 g). After a further 2 min the pressure tube was sealed with a screw cap under argon and placed in an oil bath at 60° C. for 17 h with stirring. After allowing the tube and contents to cool to room temperature, diethyl ether (15 ml) was added causing precipitation of the polymeric product. The liquid phase was decanted away and the solid residue redissolved in acetone (3 ml). The resulting acetone solution was then added dropwise to rapidly stirring diethyl ether (25 ml) and the precipitate isolated on a no. 2 sintered glass funnel with a slight burst of vacuum. The solid was washed with fresh diethyl ether (10 ml) and then allowed to dry under vacuum at room temperature (mass=1.44 g, white solid).

Step 2—Conjugation of Protein Reactive End Group to PVP-Amine:
PVP-amine (500 mg), 4-(3-tosylpropanoyl)benzoic acid (structure 6 in FIG. 3, 166 mg), and 4-dimethylaminopyridine (6 mg) were mixed with anhydrous dichloromethane (10 ml) under argon and with stirring was then added 1,3-diisopropylcarbodiimide (155 μl). The resulting mixture was allowed to stir over a weekend at room temperature. Volatiles evaporated during the weekend so the solid residue was redissolved in dichloromethane (10 ml) and then filtered though non-absorbent cotton-wool. To the filtrate was then added diethyl ether (30 ml) and the resulting precipitate isolated by centrifugation (4,600 rpm, −9° C., 10 min). The liquid phase was decanted off and the remaining residue redissolved in dichloromethane (10 ml). The diethyl ether precipitation purification method was repeated twice more and the residue allowed to dry under vacuum (513 mg). Diagnostic NMR signals for the PVP conjugated linker group occurred at 7.97, 7.82, 7.59 and 7.38 in $CDCl_3$.

Step 3—Fractionation of PVP Reagent:
A portion (120 mg) of the solid material obtained from the above step was mixed with aqueous 20 mM sodium acetate buffer, 150 mM NaCl, pH 4.0 and then centrifuged at 13,000 rpm until a clear solution was visible and the liquid phase 0.45 μm filtered. The filtrate was then fractionated (1.9 ml loaded) on a HiLoad 16/60 Superdex™ 200 prep grade size exclusion column (GE Healthcare) running 20 mM sodium acetate buffer, 150 mM, pH 4.0 at 1 ml/min by collecting fractions every 1 min during peak elution. The fraction eluting between 73.9 to 74.9 min was used for protein conjugation after freeze-drying. The peptide reaction was carried out in 100 mM sodium phosphate buffer (pH 8.0) containing 1 mM EDTA, 38 μM hydroquinone, 1.03 mM $Lam\beta1_{925-933}$ and an excess of PVP reagent. The reaction mixture was analysed by analytical RPC as described in Example 11. After one hour incubation at room temperature, approximately 60% of the free $Lam\beta1_{925-933}$ model peptide present in the reaction mixture was converted into $Lam\beta1_{925-933}$-PVP conjugate (RPC retention time of 11.3 min) successfully demonstrating that polymers other than PEG can be used.

EXAMPLE 16

Synthesis and Use of a PEG Reagent with an Amine-Based Leaving Group L

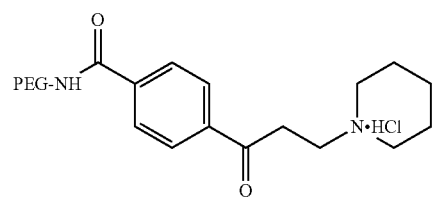

13

Synthesis Of PEG Reagent 13:
PEG reagent 13 (FIG. 19) was prepared from the direct conjugation of compound 2 (26 mg) with 5 kDa mPEG-NH2 (40 mg) in DMSO (5 ml) using DIPC (11 mg) in an analogous procedure to that of Example 1 to afford an off-white solid (31 mg). The NMR spectrum of the product (in $CDCl_3$) gave diagnostic signals at 8.02 and 7.59 ppm.

Reaction with $Lam\beta1_{925-933}$ Model Peptide of Example 11:
The reaction was carried out in 100 mM sodium phosphate buffer (pH 7.5) containing 1 mM EDTA, 38 μM hydroquinone, 1.03 mM $Lam\beta1_{925-933}$ and 3 molar equivalents of PEG reagent 13. The reaction mixture was analysed by analytical RPC as described in Example 11. Monomeric $Lam\beta1_{925-933}$ eluted at 8.1 min, dimerised $Lam\beta1_{925-933}$ eluted at 8.9 min, the amine leaving group eluted at 9.3 min, PEG reagent 13 without the amine leaving group at 15.2 min, PEG reagent 13 at 15.75 min and the product peak at 14.2 min. After 1 hour incubation at room temperature, approximately 10% of the free $Lam\beta1_{925-933}$ model peptide present in the reaction mixture was converted into $Lam\beta1_{925-933}$-PEG conjugate.

EXAMPLE 17

The Thiol PEGylation and Activity of IL-1-Ra Using PEG Reagent 9

A recombinant nonglycosylated form of the human interleukin-1 receptor antagonist (IL-1-Ra) was used as a model protein. The IL-1-Ra consists of 153 amino acids, two disulfide bonds (Cys69/Cys116 and Cys66/Cys122), has a molecular weight of 17.3 kDa and contains an N-terminal hexahistidine tag.

A series of thiol PEGylations were carried out using 1-4 molar equivalents of 10 kDa PEG reagent 9 in 50 mM sodium phosphate buffer (pH 6.0 and 7.5). Because the protein was expressed reduced, reduction of the disulfides prior to PEGylation was not necessary. The protein concentration was 0.1 mg/ml. After 1 hour incubation at 4° C., samples were taken for SDS-PAGE analysis and the result is shown in FIG. 18. At both pH 6.0 and 7.5, the main product of the PEGylation reaction was mono-PEGylated IL-1-Ra when 1 molar equivalent of PEG reagent was used. A faint band corresponding to a di-PEGylated product can also be seen, as well as a band corresponding to un-PEGylated IL1-Ra. Increasing the molar equivalents of PEG used in the reaction resulted in an increase in di-, tri- and tetra-PEGylated species. A larger scale PEGylation at pH 6.0 was then performed using 1.5 mg IR-1-Ra (0.2 mg/ml) and 1.5 molar equivalents of 20 kDa PEG reagent 9 in 50 mM sodium phosphate buffer pH 6.0 containing 20 mM EDTA. The solution was briefly vortexed and placed at 4° C. for 2 hours. The PEGylated IL-1-Ra was purified by immobilised metal affinity chromatography (IMAC) and size exclusion chromatography. Prior to IMAC, EDTA was removed by repeated cycles of concentration and dilution with fresh phosphate buffer pH 7.4 using an Amicon ultra-4 3,000 Da MWCO ultrafiltration centrifugal device (Millipore, cat. no. UFC 800324). Finally, the sample was concentrated to 4 ml and treated with 2 mM sodium borohydride for 30 minutes at room temperature followed by loading onto a HisTrap HP (1 ml) column (GE Healthcare cat. no. 17-5247-01) pre-equilibrated with phosphate buffer saline (PBS) pH 7.4. The column was washed with 20 ml PBS and elution involved a gradient from PBS to PBS containing 500 mM imidazole in 40 minutes. Fractions (1 ml) of eluate were collected and an aliquot of each fraction was analysed by SDS-PAGE to identify the fractions containing the PEGylated product. Subsequently, the fractions containing the PEGylated product were pooled together and concentrated by ultrafiltration (Amicon ultra-4 3,000 Da MWCO) to a final volume of 0.6 ml. The concentrated IMAC fractions were loaded onto a HiLoad Superdex 200 16/600 column (GE Healthcare, cat. no. 17-1069-01) which was pre-equilibrated with PBS pH 7.4. The flow rate was maintained at 1 ml/min through the run and the mono-PEGylated products eluted at about 62 min. Fractions (1 ml) were collected around the elution peak and an aliquot of each fraction was analysed by SDS-PAGE. The fractions containing pure mono-PEGylated product were concentrated by ultrafiltration and re-analysed by SDS-PAGE to confirm purity and the result is shown in Lane 2 of FIG. 19. The gel shows a single band corresponding to mono-PEGylated protein and no free protein is visible.

After quantification by UV spectrophotometry, the sample was analysed for in vitro biological activity by assessing the inhibition of IL-1β-dependent IL-6 release in MG-63 cells. MG-63 cells were added at 20,000 cells/well in 100 μl of DMEM/10% FCS. On the following day, medium was removed and 50 μl/well of fresh medium was added. Samples were added in a 5-fold dilution in duplicates (25 μl/well), pre-incubated for 1 h then IL-1β added at a final concentration of 0.3 ng/ml (25 μl/ml). The plate was incubated for a further 24 h. For assessing cell viability, 10 μl of thiozolyl blue tetrazolium bromide (MTT; 5 mg/ml in DMEM; Sigma-Aldrich cat no. M5655) was added to each well and incubated for 3 h. The plate was then centrifuged at 1,500 g for 5 min and the medium was carefully aspirated. The formazan product in metabolically active cells was then dissolved in DMSO (100 μl/well) and the absorbance was measured at 570 nm. The result is shown in FIG. 20 and shows that PEGylated IL-1Ra retained inhibitory activity after PEGylation with reagent 9.

EXAMPLE 18

PEGylation on a Polyhistidine Sequence of IL-1Ra Using PEG Reagent 9, and Activity of the PEGylated Protein The IL-1Ra of Example 17 was also PEGylated on the polyhistidine tag after oxidising the protein free cysteines to disulfides with copper sulfate prior to the PEGylation reaction as follows: Copper sulfate (1 mM) was added to 2.5 ml solution of IL-1Ra (0.6 mg/ml, 1.5 mg IL-1-Ra) in 50 mM Tris.HCl (pH 8.0) containing 200 mM NaCl. After incubation for 16 hours at 4° C., 25 mM EDTA was added and sample was loaded on to a PD-10 column (GE Healthcare) pre-equilibrated with 50 mM sodium phosphate buffer pH 7.5 containing 20 mM EDTA. The column was then eluted with 3.5 ml of fresh phosphate buffer. The protein concentration used for the PEGylation was 0.43 mg/ml and the pH 7.4 and incubated for 16 hours at 4° C. PEG reagent 9 (20 kDa) at 1.5 molar equivalents to protein. The reaction was incubated for 16 h at 4° C. The monoPEGylated species was isolated using the same chromatography as described in Example 17 along with the sodium borohydride treatment. The SDS-PAGE result of the product is shown in lane 2 of FIG. 19 where no free protein can be seen. The bioactivity of the product was assessed by measuring the inhibition of IL-1β-dependent IL-6 release in MG-63 cells as described in Example 17 and the result is shown in FIG. 20. The PEGylated IL-1Ra possessed inhibitory activity in the assay.

EXAMPLE 19

PEG Reagent Synthesis: Synthesis of 10 kDa PEG Reagent 15

PEGylated 4-(3-(2-hydroxyethylsulfonyl)propanoyl)benzoic acid reagent 15 was prepared from 4-(3-(2-hydroxyethylsulfonyl)propanoyl)benzoic acid 14 in an analogous way to that described for the synthesis of PEGylated 4-(3-tosylpropanoyl)benzoic acid 9 in Example 1, as shown in FIG. 21. Firstly, 4-(3-(2-hydroxyethylsulfonyl)propanoyl)benzoic acid 14 was prepared in an analogous way to 4-(3-tosylpropanoyl)benzoic acid but using mercaptoethanol instead of 4-methylbenzenethiol (Step 2, Example 1). NMR 14 (400 MHz) δ 3.35 (t, 2H, $COCH_2$), 3.5 (overlapping m, 4H, $CH_2SO_2CH_2$), 3.8 (t, 2H, $CH_2OH$), 5.2 (br s, $CH_2OH$), 8.05 (m, 4H, aromatic CH), 13.4 (br s, 1H, COOH). For the PEG conjugation step, the sulfone 14 (143 mg) and O-(2-aminoethyl)-O'-methyl-PEG (MW 10 kDa, 1 g, BioVectra) were dissolved in dry toluene (5 ml). The solvent was removed under vacuum without heating and the dry solid residue was then redissolved in dry dichloromethane (10 ml) under argon. To the resulting solution, cooled in an ice bath, was slowly added diisopropylcarbodiimide (DIPC, 87 mg) under argon. The reaction mixture was then kept stirring at room temperature overnight (15 h). Volatiles were then removed under vacuum (30° C., water bath) to afford a solid residue that was redissolved with gentle heating (35° C.) in acetone (45 ml). The solution was filtered over non-absorbent cotton wool to remove insoluble material. The solution was then cooled in a dry ice bath to give a white precipitate that was separated by centrifugation (4600 rpm, 30 min). The liquid phase was decanted off and this precipitation procedure was repeated three times. Afterwards the resulting off-white solid was dried under vacuum to afford the PEG reagent 15 (1 g). $^1$H NMR (400 MHz, CDCl$_3$) δ 3.30 (t, 2H, COCH$_2$), δ 3.40 (s, 3H, PEG-OCH$_3$), δ 3.40-3.85 (br m, PEG), δ 3.50 (overlapping m, 2×2H, CH$_2$SO$_2$CH$_2$), δ 3.80 (t, 2H, CH$_2$OH), δ 7.95, δ 8.05 (2×d, 2×2H, ArH of carboxylic acid moiety).

Analogous PEG reagents of different PEG molecular weights were prepared by the same general procedure. Thus, 5 kDa PEG was prepared by reaction of the sulfone 14 (256 mg), O-(2-aminoethyl)-O'-methyl-PEG (5 kDa, 1 g, Biovectra) and DIPC (174 mg) in dry dichloromethane (15 ml) affording after the acetone precipitation purification procedure an off-white solid 15 (1 g).

EXAMPLE 20

PEG Reagent Synthesis: Synthesis of 10 kDa PEG Reagent 17

PEG reagent 17 was prepared from PEG reagent 9 as follows (FIG. 22): PEG reagent 9 (10 kDa, 75 mg) was allowed to stir with mercaptosuccinic acid (6 mg) and sodium hydrogen carbonate (20 mg) in deionised water (2 ml) for approximately 18 h. Volatiles were then removed on a rotary evaporator and the solid residue redissolved in warm acetone (4 ml) with an insolubles removed by filtration through non-absorbent cotton-wool. The product was then precipitated from the acetone by cooling the solution in a dry-ice bath and then isolated by decanting off the liquid phase following centrifugation. The acetone precipitation was repeated a further three times and the solid was then dried under vacuum to give 16 (51 mg). Compound 16 (40 mg) was then oxidised to the sulfone form 17 by mixing with oxone in 1:1 methanol:water (1 ml) for approximately 18 h. The mixture was then diluted with acetone (10 ml) and insolubles were then removed by filtration under gravity through non-absorbent cotton-wool. The homogeneous filtrate was evaporated to dryness on a rotary evaporator and then redissolved in acetone (2 ml) with 2 drops of 1 N HCl added and then isolated by a single acetone precipitation as described for 16 (mg). $^1$H NMR (400 MHz, CDCl$_3$) δ 3.24-3.08 (overlapping m, CH$_2$CH, COCH$_2$), 3.38 (s, PEG-OCH$_3$), 3.44 to 3.84 (br s, overlapping m, PEG & CH$_2$SO$_2$), 4.44 (dd, SO$_2$CH), 7.45 (br s, NH), 7.98 & 8.06 (2×d, 4H, ArH of carboxylic acid moiety).

I claim:

1. A process for the conjugation of a molecule containing a thiol or amino group to a polymer, which comprises reacting said molecule with a compound of the general formula:

X—[NH—CO—Ar—W—(CH=CH)$_n$—CH=CH$_2$]$_m$ (Va)

in which X represents a polymer; W represents a keto group; n represents 0 or an integer of from 1 to 4; m represents an integer of from 1 to 8; and Ar represents an unsubstituted or substituted aryl group.

2. A process as claimed in claim 1, in which X is a polyalkylene glycol, polyvinylpyrrolidone, polyacrylate, polymethacrylate, polyoxazoline, polyvinylalcohol, polyacrylamide, polymethacrylamide, HPMA copolymer, polyester, polyacetal, poly(ortho ester), polycarbonate, poly(imino carbonate), polyamide, copolymer of divinylether-maleic anhydride and styrene-maleic anhydride, polysaccharide, or protein.

3. A process as claimed in claim 2, in which X is a polyalkylene glycol.

4. A process as claimed in claim 3, in which X is a polyethylene glycol.

5. A process as claimed in claim 1, in which n is 0.

6. A process as claimed in claim 1, in which Ar represents a phenyl group optionally substituted by one or more of the same or different substituents selected from the group consisting of alkyl, —CN, —NO$_2$, —CO$_2$R, —COH, —CH$_2$OH, —COR, —OR, —OCOR, —OCO$_2$R, —SR, —SOR, —SO$_2$R, —NHCOR, —NRCOR, —NHCO$_2$R, —NR.CO$_2$R, —NO, —NHOH, —NR.OH, —C=N—NH-COR, —C=N—NR.COR, —N$^+$R$_3$, —NH$_3$, —N$^+$HR$_2$, —N$^+$H$_2$R, halogen, —C≡CR, —C=CR$_2$ and —C=CHR, in which each R independently represents a hydrogen atom or an alkyl, aryl, or alkyl-aryl group.

7. A process as claimed in claim 6, in which Ar represents a phenyl group.

8. A process as claimed in claim 1, in which said molecule is a peptide or a protein.

9. A process as claimed in claim 1, in which the compound of formula V has the formula:

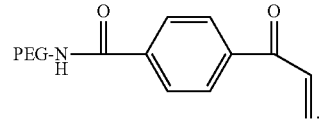

* * * * *